US008852585B2

(12) United States Patent
Scuderi, Jr. et al.

(10) Patent No.: US 8,852,585 B2
(45) Date of Patent: Oct. 7, 2014

(54) METHOD OF TREATMENT AND PROPHYLAXIS OF DISEASES RELATED TO AMYLOID DEPOSITION USING IGM

(75) Inventors: Philip Scuderi, Jr., Chapel Hill, NC (US); Afshin Safavi, Chapel Hill, NC (US); Matthew G. Langevin, Mebane, NC (US)

(73) Assignee: Grifols Therapeutics Inc., Research Triangle Park, NC (US)

( * ) Notice: Subject to any disclaimer, the term of this patent is extended or adjusted under 35 U.S.C. 154(b) by 1260 days.

(21) Appl. No.: 12/162,532

(22) PCT Filed: Jan. 30, 2007

(86) PCT No.: PCT/US2007/061269
§ 371 (c)(1),
(2), (4) Date: May 7, 2009

(87) PCT Pub. No.: WO2007/106617
PCT Pub. Date: Sep. 20, 2007

(65) Prior Publication Data
US 2009/0269359 A1    Oct. 29, 2009

Related U.S. Application Data

(60) Provisional application No. 60/763,422, filed on Jan. 30, 2006.

(51) Int. Cl.
*A61K 39/395* (2006.01)
*C07K 1/36* (2006.01)
*C07K 1/18* (2006.01)
*C07K 1/30* (2006.01)
*C07K 1/34* (2006.01)
*C07K 16/06* (2006.01)
*A61K 39/00* (2006.01)

(52) U.S. Cl.
CPC ......... *C07K 16/065* (2013.01); *A61K 39/39591* (2013.01); *A61K 2039/505* (2013.01); *A01K 2267/0312* (2013.01)
USPC ......... 424/130.1; 530/416; 530/412; 530/418

(58) Field of Classification Search
CPC ........... C07K 16/065; A61K 39/39591; A61K 2039/505; A01K 2267/0312
See application file for complete search history.

(56) References Cited

U.S. PATENT DOCUMENTS

| 5,075,425 | A | 12/1991 | Kotitschke et al. | |
|---|---|---|---|---|
| 5,554,601 | A | 9/1996 | Simpkins et al. | |
| 5,877,399 | A | 3/1999 | Hsiao et al. | |
| 6,136,312 | A | 10/2000 | Rentsch et al. | |
| 6,307,028 | B1 | 10/2001 | Lebing et al. | |
| 7,186,410 | B2 | 3/2007 | Chtourou et al. | |
| 2003/0185827 | A1* | 10/2003 | Rodriguez et al. | 424/146.1 |
| 2004/0043019 | A1* | 3/2004 | Joks et al. | 424/130.1 |

FOREIGN PATENT DOCUMENTS

| EP | 1 172 378 A | 1/2002 |
|---|---|---|
| WO | WO 96-34099 | 10/1996 |
| WO | WO 97-27296 | 7/1997 |
| WO | WO 03-097093 | 11/2007 |

OTHER PUBLICATIONS

Hurez V et al. Pooled normal human polyspecific IgM contains neutralizing anti-idiotypes to IgG autoantibodies of autoimmune patients and protects from experimental autoimmune disease. Blood, 1997; 90(10):4004-4013.*
Szabo P et al. (2008) Natural human antibodies to amyloid beta peptide. Autoimmunity Rev. 7:415-420.*
Mauch H et al. (1980) Large-scale purification of IgM from human sera: Comparison of three optimized procedures utilizing Protein a chromatography. Res. Exp. Med. (Berl) 177:33-41.*
Nikolayenko IV et al. (2005) Preparation of highly purified human IgG, IgM, and IgA for immunization and immunoanalysis. Ukrainica Bioorganica Acta, 2:3-11.*
Amiel, S., "Metabolism, Amylin and Diabetes," *Lancet* 341:1249-1250 (1993).
Buchwald, H., et al., "Long-term, Continuous Intravenous Heparin Administration by an Implantable Infusion Pump in Ambulatory Patients with Recurrent venous Thrombosis," *Surgery* 88:507 (1980).
Cooper, G.J.S., et al., "Amylin Found in Amyloid Deposits in Human Type 2 Diabetes Mellitus May be a Hormone that Regulates glycogen Metabolism in Skeletal Muscle," *Proc. Natl. Acad. Sci. USA* 85:7763-7766 (1988).
Cooper, G.J.S., et al., "Purification and Characterization of a Peptide from Amyloid-Rich Pancreases of Type 2 Diabetic Patients," *Proc. Natl. Acad. Sci. USA* 84:8628-8632 (1987).
Coria, F. et al., "isolation and Characterization of Amyloid P Component from Alzheimer's Disease and Other Types of Cerebral Amyloidosis," *Lab. Invest.* 58:454-8 (1988).
Dodel, R., et al., "Human Antibodies Against Amyloid Beta Peptide: A Potential Treatment for Alzheimer's Disease," *Ann. Neurol.*, 52(2):253-256 (2002).
Dodel, R., et al., "Intravenous Immunoglobulins containing antibodies against b-amyloid for the treatment of Alzheimer's disease," *J. Neurol. Neurosurg. Psychiatry*, 75:1472-1474 (2004).
During, M.J., et al., "Controlled Release of Dopamine from a polymeric Brain Implant: In Vivo Characterization," *Ann. Neurol.* 25:351-356 (1989).
Frangione, B., "Systemic and Cerebral Amyloidosis," *Ann. Med.* 21:69-72 (1989).
Fraser, P.E., et al., "Fibril Formation by Private, Rodentm, and Dutch-Hemorrhagic Analogues of Alzherimer Amyloid B-Protein," *Biochem.* 31: 10716-10723 (1992).
Frautschy, S.A., et al., "The Microglial Response to Amyloid Plaques in APPsw Transgenic Mice," *Am. J. Pathol.* 152(1): 307-317 (1998).

(Continued)

*Primary Examiner* — Kimberly A Ballard
(74) *Attorney, Agent, or Firm* — Womble Carlyle Sandridge & Rice LLP

(57) ABSTRACT

The invention relates to a method of treating or preventing disease associated with β-amyloid polypeptides comprising administration of an immunoglobulin preparation enriched in immunoglobulin M (IgM), and pharmaceutical compositions comprising such preparations.

10 Claims, 13 Drawing Sheets

(56) References Cited

OTHER PUBLICATIONS

Glenner, G. and C. Wong, "Alzheimer's Disease: Initial Report of the Purification and xharacterization of a Novel Cerebrovascular Amyloid Protein," *Biochem. Biophys. Res. Commun.*, 120:885-890 (1984).
Glenner, G. and C. Wong, "Alzherimer's Disease and Down's Syndrome: Sharing of a unique Cerebrovascular Amyloid Fibril Proteins," *Biochem. Biophys. Res. Commun.* 122:1131-1135 (1984).
Glenner, G. and M. Murphy, "Amyloidosis of the Nervous System," *J. Neurol. Sci.* 94:1-28 (1989).
Goldgaber, D. et al., "Characterization and Chromosomal Localization of a cDNA Encoding Brain Amyloid of Alzheimer's Disease," *Science* 235:8778-8780 (1987).
Goodson, J.M., "Dental Applications," *Medicol Applications of Controlled Releose*, 2.115-138 (1984).
Haan, J. and R.A.C. Roos, "Amyloid in Central Nervous System Disease," *Clin. Neurol. Neurosurg.* 92(4):305-310 (1990).
Haan, J., et al., "Dementia in hereditary Cerebral Hemmorrhage with Amyloidosis—Dutch Type," *Arch. Neurol.* 47:965-967 (1990).
Haan, J., et al., "Progressive Dementia, Without Cerebral Hemmorrhage, in a Patient with Hereditary Cerebral Amyloid Angiopathy," *Clin. Neuro. Neurosurg.* 94: 317-318 (1992).
Hack, C.E., et al., "Intravenous Immunoglobulins: A Treatment for Alzheimer's Disease?" *J. Neurology, Neurosur. and Psych.*, 75(10): 1374-1375 (2004).
Howard, M. A., et al., "Intracerebral Drug Delivery in rats with Lesion-Induced Memory Deficits," *J. Neurosurg.* 71:105-112 (1989).
Hsiao, K. et al., et al., "Correlative Memory Deficits, Aβ Elevation, and Amyloid Plaques in Transgenic Mice," *Science* 274:99-102 (1996).
Irizarry, M.C., et al., "$App_{sw}$ Transgenic Mice Develop Age-Related Aβ Deposits and Neuropil Abnormalities, but No Neuronal Loss in CA1," *J. Neuropathol. Exp. Neurol.* 56(9):965-973 (1997).
Kang, J., et al., "The Precursor of Alzheimer's Disease Amyloid A4 Protein Resembles a Cell-Surface Receptor," *Nature* 325:733-736 (1987).
Khole, V., et al., "Identification of Epididymis Specific Antigen by Neonatal Tolerization," *Am. J. Repro. Immunol.* 44:350-356 (2000).
Klunk, W., et al., "Staining of AD and Tg2576 oMuse Brain with X-34, a Highly Fluorescent Derivative of Chrysamine G and a Potential In Vivo Probe for b-Sheet Fibrils," *Soc. Neurosci. Abstr.* 23:1638 (1997).
Langer, R. and N. Peppas, "Chemical and Physical Structure of polymers as Carriers for Controlled release of Bioactive Agents: A Review," *J. Macromol. Chem.*, 23(1): 61-126 (1983).
Langer, R., "New Methods of Drug Delivery," *Science* 249:1527-1533 (1990).
Langer, R.S. and D.L. Wise, "Medical Applications of Controlled Release," *CRC Press* (1937).
Levy, E., et al., "Mutation of the Alzheimer's Disease Amyloid Gene in Hereditary Cerebral Hemorrhage, Dutch type," *Science* 248:1124-26 (1990).
Levy, R., et al., "Inhibition of Calcification of Bioprosthetic Heart valves by Local Controlled-Release Diphosphate," *Science* 228:190-192 (1985).
Levy, Y., et al., "Intravenous Immunoglobulins in Peripheral Neuopathy Associated with Vasculitis," *Animals of the Rheumatic Diseases*, 62(12): 1221-1223 (2003).
Lopez-Berestein, G., "Treatment of Systemic Fungal Infections with Liposomal-Amphotericin B," *Liposomes in the Therapy of Infectious Disease and Cancer*, 317-327 (1989).
Pappolla, M.A., et al., "Evidence of Oxidative Stress and in Vivo Neurotoxicity of β-Amyloid in a Transgenic Mouse Model of Alzheimer's Disease," *Am. J. Pathol.* 152:871-877 (1998).
Prelli, F. et al., "Expression of a Normal and Variant Alzheimer's B-Protein Gene in Amyloid of Hereditary Cerebral Hemorrhage, Dutch Type: DNA and Protein Diasgnostic Assays," *Biochem. Biophys. Res. Commun.* 170:301-307 (1990).
Robakis, N,. et al., "Molecular Cloning and Characterization of a cDNA Enclosing the Cerebrovascular and the Neuritic Plaque Amyloid Peptides," *Proc. Natl. Acad. Sci. USA* 84:4190-4194 (1987).
Roos, R.A., et al., "Hereditary Cerebral Hemorrhage with Amyloidosis—Dutch Type: A Congophilic Angiopathy," *Ann. N.Y. Acad. Sci.* 640:155-60 (1991).
Rozemuller, A., et al., "Distribution of B/A4 Protein and Amyloid Precursor Protein in Hereditary Cerebral Hemmorrhage with Amyloidosis—Dutch Type and Alzheimer's Disease," *Am. J. Pathol.* 142(5):1449-57 (1993).
Saudek, C.D., et al., "A Preliminary Trial of the Programmable Implantable Medication System for Insulin Delivery," *N. Engl. J. Med.* 574-579 (1989)).
Sefton, M.V., "Implantable Pumps," *CRC Crit. Ref. Biomed. Eng.* 14(3):201-240 (1987).
Sigounas, G., et al., "Half-Life of Polyreactive Antibodies," *J. Clin. Immunol.*, 14(2):134-140 (1994).
Smolen, V.F. and L. Ball, *Controlled Drug Bioavailability, Drug Product Design and Performance* (eds.), Wiley: N.Y. (1984).
Tanzi, R.E., et al., "Amyloid B Protein Gene: cDNA, mRNA Distribution, and Genetic Linkage Near the Alzheimer Locus," *Science* 235:880-884 (1987).
Timmers, W.F., et al., "Parenchymal Preamyloid and Amyloid Deposits in the Brains of Patients with Hereditary Cerebral Hemorrhage with Amyloidosis—Dutch type," *Neurosci. Lett.* 118:223-226 (1990).
Treat, J., et al., "Liposome Encapsulated Doxorubicin Preliminary Results of Phase I and II Trials," *Liposomes in the Therapy of Infectious Disease and Cancer*, 353-365 (1989).
Westermark, P., et al., "Amyloid Fibrils in Human Insulinoma and Islets of Langerhans of the Diabetic Cat are Deried from a Neuropeptide-like Protein also Present in Normal Islet Cells," *Proc. Natl. Acad. Sci. USA* 84:3881-3885 (1987).
Westermark, P., et al., Islet Amyloid in Type 2 Human Diabetes Mellitus and Adult Diabetic Cats Contains a Novel Putative Polypeptide Hormone,: *Am. J. Physiol.* 127:414-417 (1987).
Wisniewski, T., et al., "Peptides Homologouous to the Amyloid Protein of Alzheimer Disease Contaiing a Glutamine for Glutamic Acid Substitution Have Accelerated Amyloid Fibril Formation," *Biochem. Biophys. Res. Commun.* 179:1247-1254 (1991).
Wisniewski, T., et al., "Peptides Homologouous to the Amyloid Protein of Alzheimer Disease Contaiing a Glutamine for Glutamic Acid Substitution Have Accelerated Amyloid Fibril Formation," *Biochem. Biophys. Res. Commun.* 180:1528 (1991).

\* cited by examiner

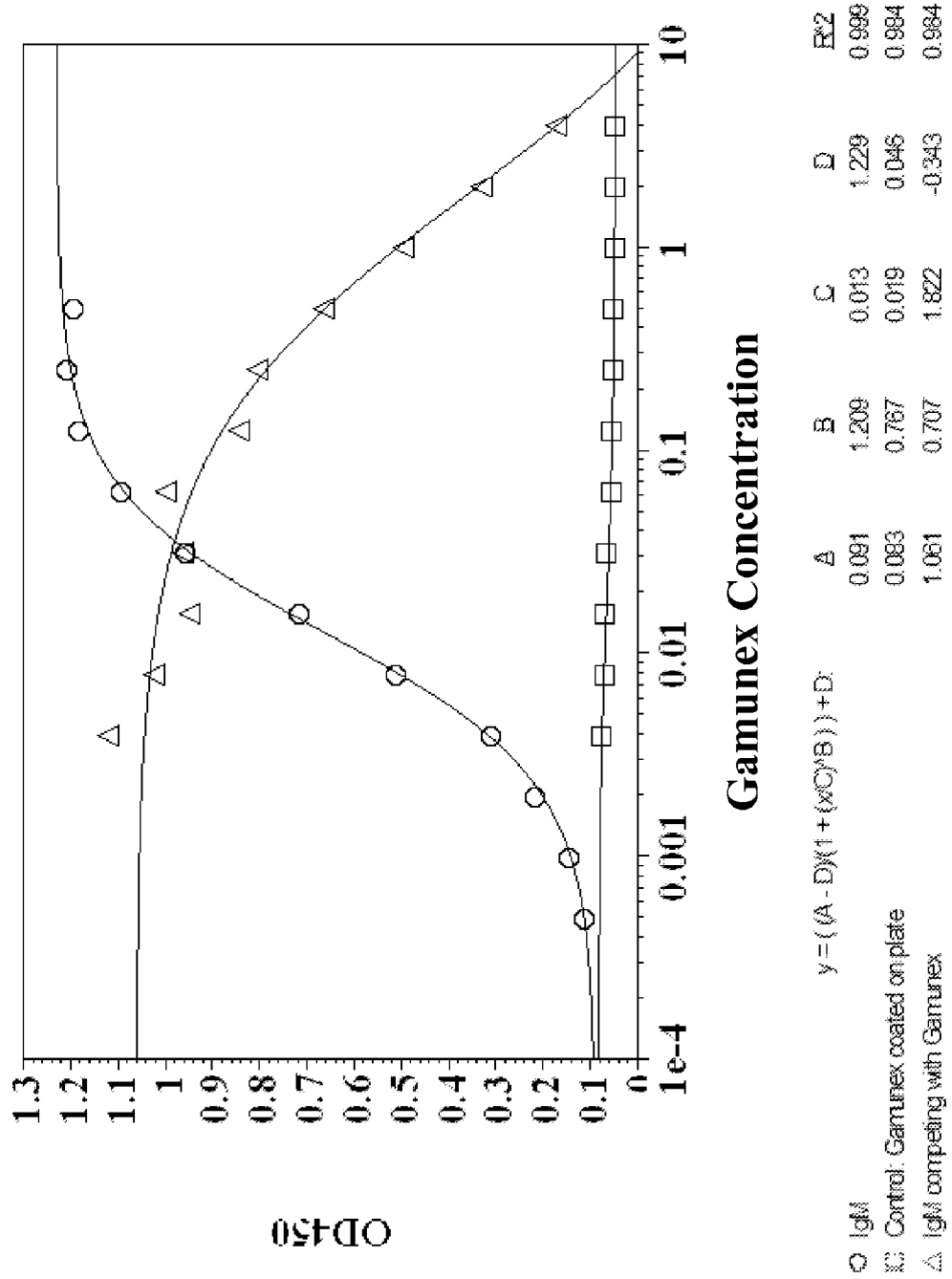

METHOD OF TREATMENT AND PROPHYLAXIS OF DISEASES RELATED TO AMYLOID DEPOSITION USING IGM

RELATED APPLICATIONS

The present application is a National Phase Application under §371 of International Application Serial Number PCT/US07/061269 filed on Jan. 20, 2007, which claims benefit of priority to Provisional Application Ser. No. 60/763,422, filed on Jan. 30, 2006 the contents of which are herein incorporated by reference in its entirety.

BACKGROUND OF THE INVENTION

Amyloid β (Aβ) 1-42 peptide is believed to be one of the key factors in development and progression of Alzheimer's disease. While the exact pathogenic role of amyloid β-peptide in Alzheimer's disease has not yet been definitely established, accumulating evidence supports the hypothesis that amyloid β-peptide production and deposition in the brain is a causative event in Alzheimer's disease. Therefore, the problem of production, accumulation, and clearance of amyloid β-peptide in the brain has emerged as one of the possible rational approaches for the treatment of Alzheimer's disease.

It has been recently found that intravenous IgG preparations contain antibodies specific to Aβ 1-42 amyloid peptide. Also, in two small human trials, intravenous IgG was found to slow down the progression of Alzheimer's disease (Dodel, R., et al., "Intravenous Immunoglobulins containing antibodies against b-amyloid for the treatment of Alzheimer's disease," *J. Neurol. Neurosurg. Psychiatry*, 75:1472-1474 (2004); and Dodel, R., et al., "Human antibodies against amyloid beta peptide: A potential treatment for Alzheimer's disease," *Ann. Neurol*, 52:253-256 (2002)). Although the mechanism of action of IgG in this indication remains to be elucidated, the authors speculated that the simple systemic removal of the offensive Aβ 1-42 peptide might be the reason for the efficacy of intravenous IgG.

Immunoglobulin M (IgM) is the immunoglobulin found in third largest concentration in the serum of most animals (about 6-10% of total immunoglobulin pool). Normal plasma concentrations of IgM in humans are from about 0.6 to about 2.5 mg/ml for males and from about 0.7 to about 2.8 mg/ml for females.

IgM is a 19S molecule with a molecular weight of 950 kDa and is made up of five identical 180 kDa subunits. Each of these subunits is similar in structure to the monomer of IgG, except they possess four, rather than three, $C_H$ domains. The IgM monomers are linked by disulfide bonds in a circular fashion to form a star, and a small cysteine-rich polypeptide called the J-chain (20 kDa) links two of the units (see FIG. 1). IgM molecules are secreted intact by plasma cells, and the J-chain must therefore be considered to be an integral part of this molecule. The plasma half-life of IgM is about 5.1 days.

IgM is the major immunoglobulin isotype produced in a primary immune response. It is also produced in a secondary response, but this tends to be masked by the predominance of IgG. Although produced in a relatively small quantity, IgM, due to its pentameric structure, is considerably more efficient (on a molar basis) than IgG at complement activation, opsonization, neutralization of viruses, and agglutination. Most of the isoagglutinins in human serum, which recognize blood type antigens A and B, are of the IgM class. Therefore, some special measures may be utilized during purification to remove isoagglutinins and make the preparation more compatible with A and B blood types.

Passive immunization using IgM-containing immunoglobulin preparations can provide advantages in the treatment and/or prevention of disorders or diseases associated with amyloid peptides.

SUMMARY OF THE INVENTION

The present invention related to methods for treating or preventing (including any clinically significant decrease in symptoms or slowing of the progression of the disease, respectively) amyloid-associated disease. The invention also relates to immunoglobulin preparations useful in such methods.

Accordingly, in one aspect, the invention relates to a method of treating or preventing a disease associated with β-amyloid polypeptides comprising administration of an immunoglobulin preparation produced from pooled human plasma samples as starting material, wherein the immunoglobulin preparation is enriched in immunoglobulin M (IgM). The immunoglobulin preparation can comprise at least about 80% IgM or at least about 90% IgM. The immunoglobulin preparation comprises IgM antibodies that bind specifically to Aβ 1-42. In some embodiments, the disease associated with β-amyloid polypeptides is chronic inflammatory illnesses, multiple myeloma, macroglobulinernia, familial amyloid polyneuropathy (Portuguese) and cardiomyopathy (Danish), systemic senile amyloidosis, familial amyloid polynephropathy (Iowa), familial amyloidosis (Finnish), Gerstmann-Straussler-Scheinker syndrome, familial amyloid nephropathy with urticaria and deafness (Muckle-Wells syndrome), medullary carcinoma of thyroid, isolated atrial amyloid, and hemodialysis-associated amyloidosis (HAA), sporadic cerebral amyloid angiopathy, hereditary cerebral amyloid angiopathy, Downs syndrome, Parkinson-dementia of Guam, age-related asymptomatic amyloid angiopathy, hereditary cerebral hemorrhage with amyloidosis, or Alzheimer's disease. The disease associated with β-amyloid polypeptides can be an amyloid-associated neurodegenerative disease. The disease can be Alzheimer's disease.

In some embodiments, the immunoglobulin preparation can be administered at a dosage of immunoglobulin from about 0.1 μg per kg body weight to about 1000 mg per kg body weight. The immunoglobulin preparation also can be administered at a dosage of from about 0.5 μg per kg body weight to about 500 mg per kg body weight; from about 0.5 μg per kg body weight to about 100 mg per kg body weight; or from about 5 μg per kg body weight to about 50 mg per kg body weight.

In another aspect, the invention relates to a pharmaceutical composition comprising IgM, at least a portion of which binds specifically to Aβ 1-42, where the IgM can be prepared from starting material comprising immunoglobulins and other substances by adjusting the pH of the starting material to form an intermediate solution comprising dissolved immunoglobulins, adjusting the intermediate solution of step a) to conditions of pH, temperature, and caprylate concentration such that a first precipitate and a first supernatant comprising immunoglobulins are formed, separating the first supernatant from the first precipitate, incubating the first supernatant under conditions of time, pH, temperature and caprylate concentration such that a second precipitate and a second supernatant comprising immunoglobulins are formed, separating the second supernatant from the second precipitate, contacting the second supernatant with a first anion exchange resin under conditions of pH and ionic strength such that substantially none of the immunoglobulin G or immunoglobulin M is bound to the first resin but immunoglobulin A and other substances are bound to the first resin, separating a fraction containing substantially all of the immunoglobulin G and immunoglobulin M from the result of the previous step, contacting the immunoglobulin G and M with a second anion exchange resin under conditions of pH and ionic strength such that substantially none of the immunoglobulin G is bound to the second resin but immunoglobulin M and other substances are bound to the second resin, eluting IgM from the second anion exchange resin column with a buffered solution having a conductivity in the range of that found in a solution of at least 100 mM sodium chloride, applying the IgM to a gel filtration resin and recovering the IgM, applying the IgM to an affinity resin comprising immobilized antigens A and B, and recovering the IgM. The starting material can be derived from pooled human blood products. The pooled human blood products can be collected from donors that have not been screened to determine their anti-Aβ immunoglobulin titer.

BRIEF DESCRIPTION OF THE DRAWINGS

FIG. 5 is a graph illustrating inhibition of IgM binding to Aβ-coated plates by competing GAMUNEX.

DETAILED DESCRIPTION OF EMBODIMENTS OF THE INVENTION

Figure 1:
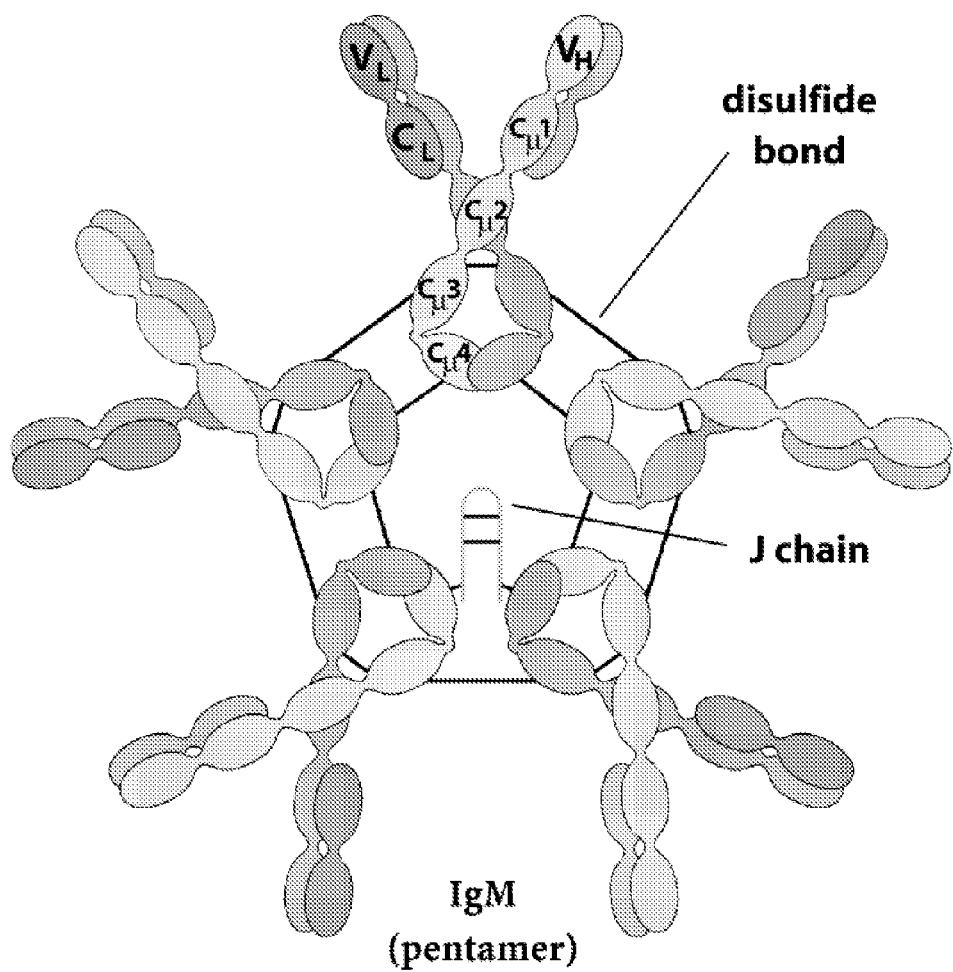
FIG. 1 is a schematic drawing illustrating the overall pentameric structure and features of the individual subunits.

The present invention relates to the discovery that IgM-containing immunoglobulin preparations derived from pooled human plasma comprise IgM that binds specifically to β amyloid peptides. In certain aspects, the invention provides immunoglobulin preparations and methods useful for the treatment and/or prophylaxis of diseases and disorders associated with amyloidosis, including Alzheimer's disease.

Compositions or methods "comprising" one or more recited elements may include other elements not specifically recited. For example, a composition that comprises IgM can encompass immunoglobulins of other types, and can include other proteinaceous and non-proteinaceous substances.

As used herein, the term "about" or "approximately" means that a value can fall within a scientifically acceptable range for that type of value, which also will depend on how quantitative a measurement of the value can be achieved given the available tools of measurement.

The terms "antibody" and "immunoglobulin" are used interchangeably herein, unless otherwise indicated expressly.

Diseases and Disorders Associated with Amyloidosis

A neurodegenerative disease or disorder is associated with amyloidosis when amyloid deposits or amyloid plaques are found in or in proximity to tissues affected by the disease, or when the disease is characterized by overproduction of a protein, particularly an amyloid protein, that is or can become insoluble. The amyloid plaques can provoke pathological effects directly or indirectly by known or unknown mechanisms. Examples of amyloid diseases include, but are not limited to, systemic diseases, such as chronic inflammatory illnesses, multiple myeloma, macroglobulinernia, familial amyloid polyneuropathy (Portuguese) and cardiomyopathy (Danish), systemic senile amyloidosis, familial amyloid polynephropathy (Iowa), familial amyloidosis (Finnish), Gerstrnann-Straussler-Scheinker syndrome, familial amyloid nephropathy with urticaria and deafness (Muckle-Wells syndrome), medullary carcinoma of thyroid, isolated atrial amyloid, and hemodialysis-associated amyloidosis (HAA); and amyloid-associated neurodegenerative diseases.

As noted above, in addition to systemic amyloidosis, the present invention relates particularly to neurodegenerative diseases involving amyloidosis. The term "neurodegenerative disease" refers to a disease or disorder of the nervous system, particularly involving the brain, that manifests with symptoms characteristic of brain or nerve dysfunction, e.g., short-term or long-term memory lapse or defects, dementia, cognition defects, balance and coordination problems, and emotional and behavioral deficiencies. Such diseases are "associated with amyloidosis" when histopathological (biopsy) samples of brain tissue from subjects who demonstrate such symptoms reveal amyloid plaque formation. Because biopsy samples from brain, especially human brain, are obtained with great difficulty from living subjects or might not be available at all, the association of a symptom or symptoms of neurodegenerative disease with amyloidosis often is based on criteria other than the presence of amyloid deposits in a biopsy sample. Thus, particularly with respect to Alzheimert's disease (AD), traditional diagnosis depends on symptomology and, if relevant, family history. In clinical practice, a physician will diagnose AD on the basis of symptoms of senile dementia, including cognitive dysfunction, retrograde amnesia (loss of memory for recent events), progressive impairment of remote memory, and possibly depression or other neurotic syndromes. The individual presents with slow disintegration of personality and intellect. Imaging may reveal large cell loss from the cerebral cortex and other brain areas. AD differs from senile dementia, however, by age of onset: AD is likely to occur in the fifth or sixth decade, whereas senile dementia occurs in the eighth decade or later.

In a specific embodiment according to the present invention, the neurodegenerative disease associated with amyloidosis is AD, a condition that includes sporadic AD, ApoE4-related AD, other mutant APP forms of AD (e.g., mutations at APP717, which are the most common APP mutations), mutant PS1 forms of familial AD (FAD) (see, WO 96/34099), mutant PS2 forms of FAD (see, WO 97/27296), and α-2-macroglobulin-polymorphism-related AD. In other embodiments, the disease can be the rare Swedish disease characterized by a double KM to NL mutation in amyloid precursor protein (APP) near the amino-terminus of the βAP portion of APP (Levy et al., *Science* 248:1124-26 (1990)). Another such disease is hereditary cerebral hemorrhage with amyloidosis (HCHA or HCHWA)-Dutch type (Rozemuller et al., *Am. J. Pathol.* 142:1449-57 (1993); Roos et al., *Ann. N.Y. Acad. Sci.* 640:155-60 (1991); Timmers et al., *Neurosci. Lett.* 118:223-6 (1990); Haan et al., *Arch. Neurol.* 47:965-7 (1990)). Other such diseases known in the art and within the scope of the present invention include, but are not limited to, sporadic cerebral amyloid angiopathy, hereditary cerebral amyloid angiopathy, Downs syndrome, Parkinson-dementia of Guam, and age-related asymptomatic amyloid angiopathy (see, e.g., Haan and Roos, *Clin. Neurol. Neurosurg.* 92:305-310 (1990); Glenner and Murphy, N. *Neurol. Sci.* 94:1-28 (1989); Frangione, *Ann. Med.* 21:69-72 (1989); Haan et al., *Clin. Neuro. Neurosurg* 94:317-8 (1992); Fraser et al., *Biochem.* 31:10716-23 (1992); Coria et al., *Lab. Invest.* 58:454-8 (1988)). The actual amino acid composition and size of the βAP (beta-amyloid peptide) involved in each of these diseases can vary, as is known in the art (see above, and Wisniewski et al., *Biochem. Biophys. Res. Commun.* 179:1247-54 (1991) and *Biochem. Biophys. Res. Commun.* 180:1528 (1991) [published erratum]; Prelli et al., *Biochem. Biophys. Res. Commun.* 170:301-307 (1990); Levy, et al., *Science* 248: 1124-26 (1990)).

Amyloid

The terms "amyloid," "amyloid plaque," and "amyloid fibril" refer generally to insoluble proteinaceous substances with particular physical characteristics independent of the composition of proteins or other molecules that are found in the substance. Amyloid can be identified by its amorphous structure, eosinophilic staining, changes in thioflavin fluorescence, and homogeneous appearance. Protein or peptide components of amyloid are termed herein "amyloid polypeptides," and include, but are not limited to, β-amyloid peptide (Aβ), including synthetic βAPs corresponding to the first 28, 40, or 42 amino acids of Aβ, i.e., Aβ 1-28, Aβ 1-40, Aβ 1-42, respectively, as well as a synthetic βAP corresponding to amino acids 25-35 of Aβ, i.e., Aβ 25-35. Other amyloid peptides include scrapie protein precursor or prion protein (associated with Creuzfeldt-Jacob's disease); synuclein (associated with Parkinson's disease), Huntington's protein (associated with Huntington's chorea), immunoglobulin, including κ or λ light or heavy chains, or fragments thereof, produced by myelomas; serum amyloid A; β2-microglobulin; ApoA1; gelsolin; cystatin C; (pro)calcitonin; atrial natriuretic factor; islet amyloid polypeptide, also known as amylin (see, Westermark et al., *Proc. Natl. Acad. Sci. USA* 84:3881-85, 1987; Westermark et al., *Am. J. Physiol.* 127:414-417, 1987; Cooper et al., *Proc. Natl. Acad. Sci. USA* 84:8628-32, 1987; Cooper et al., *Proc. Natl. Acad. Sci. USA* 85:7763-66, 1988; Amiel, *Lancet* 341:1249-50, 1993); and the like. In a specific aspect, the term "amyloid" is used herein to refer to substances that contain Aβ. "Amyloidosis" refers to the in vivo deposition or aggregation of proteins to form amyloid plaques or fibrils.

The 42 amino acid (4.2 kDa) β-Amyloid Peptide (Aβα1-42 or βAP) derives from a family of larger Amyloid Peptide Precursor (APP) proteins (Glenner and Wong, *Biochem. Biophys. Res. Commun.* 120:885-890 (1984); Glenner and Wong, *Biochem. Biophys. Res. Commun.* 122:1131-35 (1984); Goldgaber et al., *Science* 235:8778-8780 (1987); Kang et al., *Nature* 325:733-736 (1987); Robakis et al., *Proc. Natl. Acad. Sci. USA* 84:4190-4194 (1987); Tanzi et al., *Science* 235:880-884 (1987)). APP 25 is a transmembrane protein found in a number of isoforms, which in general are referred to herein as full length APP (flAPP). In addition, there is a soluble form of APP (sAPPα), formed by the action of α-secretase.

The "level of Aβ" in a biological sample can be detected by any method known in the art, including by not limited to immunoassay, biochemical analysis (e.g., purification, gel electrophoresis, quantitative amino acid sequence analysis or composition analysis, Congo red or Thioflavin-T staining, and the like), or other methods known to detect Aβ. In particular, fluorescence methods using Thioflavin T are used to detect aggregated peptide. A "biological sample" includes, but is not limited to body fluids (blood, blood cells, plasma, serum, cerebrospinal fluid, urine), tissues (e.g., spinal chord, nerves, etc.), or organs (preferably brain, but also including liver, kidney, pancreas, etc.).

Assays for anti-β amyloid antibody can be accomplished by techniques known in the art, e.g., radioimmunoassay, ELISA (enzyme-linked immunosorbant assay), "sandwich" immunoassays, immunoradiometric assays, gel diffusion precipitation reactions, immunodiffusion assays, in situ immunoassays (using colloidal gold, enzyme or radioisotope labels, for example), Western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of an amyloid peptide, one can assay generated hybridomas for a product which binds to an amyloid peptide fragment containing such epitope.

Immunoglobulin Preparations

The present invention relates to the discovery that IgM purified from donated, pooled human sources exhibits specificity toward Aβ 1-42 peptide. In one aspect, IgM-containing immunoglobulin preparations can be prepared in accordance with U.S. Pat. No. 6,307,028 to Lebing, et al., fully incorporated herein by reference.

Lebing, et al. disclose a process for preparation of IVIG which includes an anion exchange chromatographic step, where this resin retains most of the IgM of the starting materials. According to the present invention, IgM is eluted from this anion exchange resin, and subjected to gel filtration, followed by isoagglutinin removal by passing the preparation through a resin comprising immobilized synthetic antigen A and B.

Oligomerization of IgM is reduced by processing at low concentrations, at relatively low pH, and by minimizing exposure of IgM to high salt. Final preparations are formulated at 0.2 M glycine (pH 4.2) to further avoid oligomerization. Further details regarding preparation of IgM according to the invention are provided in Example 1 below. However, it should be recognized that specific examples herein are only illustrative of the invention, and none are intended to be limiting of the scope of the invention as claimed.

Aβ Peptide Binding

To determine IgM binding to Aβ peptides, an ELISA assay to quantify anti-Aβ 1-42 in the IgM pool was developed. In this assay, a microtiter plate was coated with synthetic peptide Aβ 1-42, its shortened version Aβ 22-35, as well as an irrelevant protein α1-protease inhibitor, and varying concentrations of pooled, plasma-derived IgM were added to the plate.

Bound IgM was detected using goat anti-human IgM conjugated with horseradish peroxidase. IgM showed a high and saturated binding to the full-size amyloid peptide (FIG. 2), whereas very little or no binding was detected for the truncated peptide or α1-protease inhibitor.

In order to test whether the observed binding was specific, a control experiment was performed in which the IgM preparation was incubated overnight with SEPHAROSE beads covalently coated with Aβ 1-42 peptide. As a negative control, the IgM preparation was also incubated with uncoated SEPHAROSE beads under the same conditions. The immunodepleted material was tested for binding to Aβ 1-42. The IgM preparation incubated with uncoated SEPHAROSE beads showed good binding on wells coated with Aβ 1-42 and no binding on wells coated with α1PI. However, IgM incubated with Aβ 1-42 coated beads exhibited very little binding on wells coated with Aβ 1-42 (FIG. 3), indicating that binding of IgM to amyloid peptide Aβ 1-42 is specific.

Figure 4A:
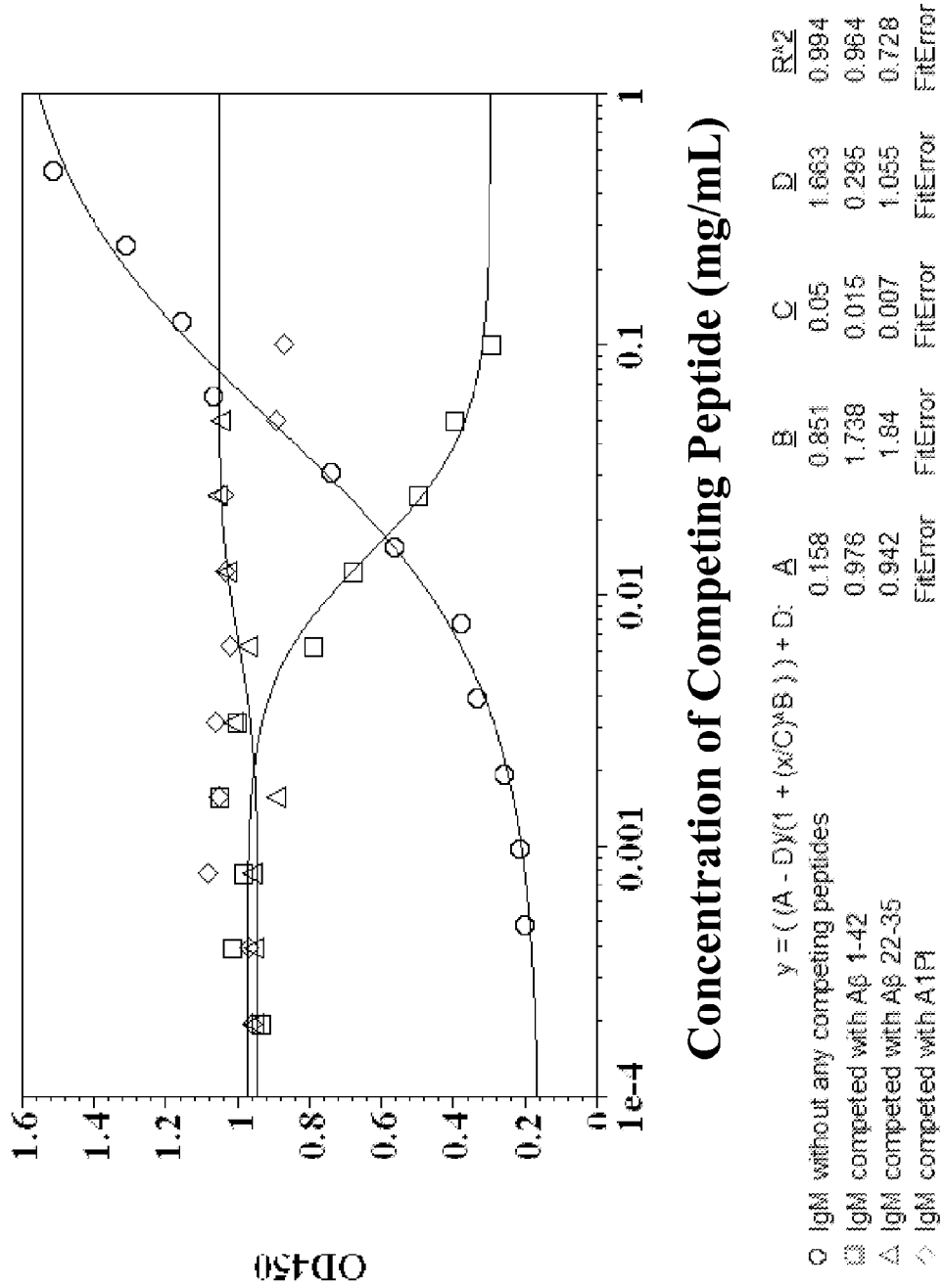
FIGS. 4A and 4B are graphs illustrating inhibition of IgM binding to Aβ-coated plates by various Aβ-related and unrelated peptides.
Figure 4B:
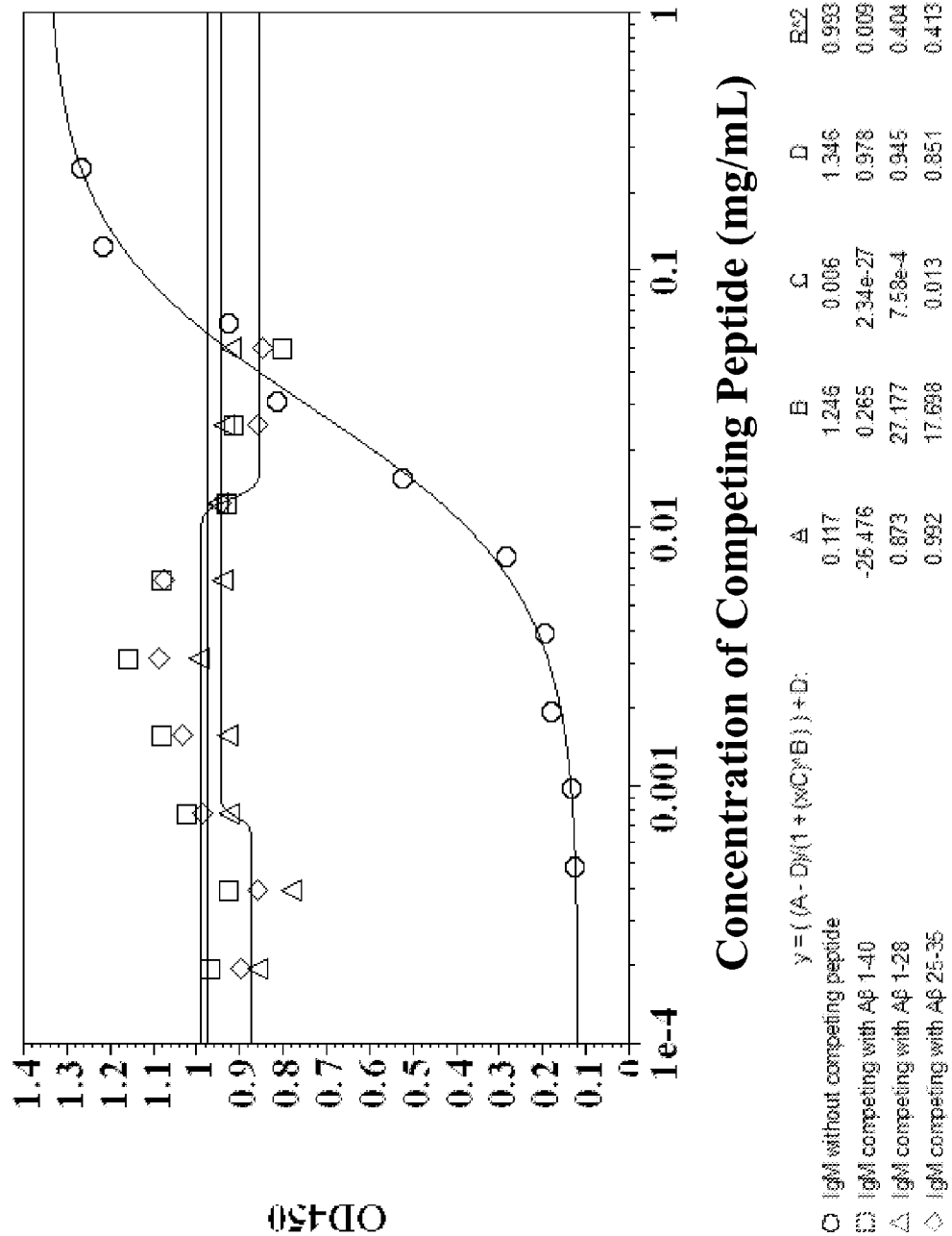

To further confirm that IgM binding to Aβ 1-42 peptide is specific, a series of peptide competition experiments were performed to look for inhibitions of the ELISA signal. Varying concentrations of free Aβ 1-42 and its smaller derivatives (Aβ 22-35, 1-40, 1-28, 25-35) and an unrelated protein, α1PI, were pre-incubated with 0.1 mg/ml IgM for 1 hour and then added to Aβ 1-42 coated plates. Full length Aβ peptide was the only competitor able to block IgM binding to the plate (FIGS. 4A and 4B). This effect was concentration-dependent with 0.1 mg/ml of the free Aβ 1-42 peptide being able to inhibit binding of IgM to the ELISA plate completely.

None of Aβ 1-42 peptide derivatives, such as Aβ 1-28, Aβ 25-35, or even the Aβ 1-40 peptide, were able to compete for the IgM binding. Without wishing to be bound by any particular theory, these results may indicate that either: 1) the IgMs against Aβ 1-42 require the peptide to be in a particular confirmation; or 2) that the epitope recognition site is in the C-terminal portion of the peptide.

To further evaluate the specificity and binding of human IgM pool, a competition experiment was set up between human IgG pool (GAMUNEX, Talecris Biotherapeutics, Research Triangle Part, N.C.) and the IgM pool. Various dilutions of GAMUNEX were prepared and mixed with 0.1 mg/ml IgM. Next, these mixtures were added to an Aβ 1-42 coated plate. 4 mg/ml GAMUNEX completely abolished IgM binding (FIG. 5). This experiment suggests that the IgM pool may share some common epitopes with the IgGs found in plasma against Aβ 1-42. The series of inhibition experiments, combined with the immunodepletion data, confirm binding of IgM to the β-amyloid peptide Aβ 1-42, and that the binding is specific.

Further, fragments of IgM generated using 2-mercaptoethylamine (MEA—see FIG. 6 and Example 6 below) were tested for binding to Aβ 1-42 peptides. The newly generated IgM fragments were diluted and added to Aβ 1-42 and α1PI coated wells to test for binding and specificity. The IgG-type fragments retained their binding and specificity characteristics, similar to the pentomeric IgM (see FIG. 8).

The discovery that pooled IgM contains antibody against β-amyloid peptide Aβ 1-42 indicates that this immunoglobulin can be useful for the management of Alzheimer's disease. Intravenously delivered IgM can be used prophylactically, in individuals susceptible to Alzheimer's disease, or for treatment of patients diagnosed with Alzheimer's disease. Further, monomeric IgM (produced as a result of mild reduction of disulfides connecting all five subunits with the J-chain), or low-molecular weight derivatives of IgM (for example, proteolytic fragments of IgM) can also be used for management of Alzheimer's disease. In fact, smaller IgM fragments may pass the brain blood barrier more efficiently and, therefore, be more potent than full length IgM. Such IgM derivatives can be tested according to the methods and procedures disclosed herein for retention of binding and selectivity toward Aβ 1-42 and Aβ-related peptides.

The term "patient" includes human and other mammalian subjects that receive either prophylactic or therapeutic treatment.

Pharmaceutical Compositions and Administration

Individuals with normal levels of anti-amyloid antibodies appear to be protected from neurodegenerative disease. However, clinical testing of an Aβ 1-42 peptide vaccine has resulted in brain inflammation in a number of patients. Accordingly, delivery of natural anti-amyloid antibodies, i.e., passive immunization, to subjects at risk for or suffering from a neurodegenerative disease, e.g., AD, has greater potential for safety as well as efficacy. Immunoglobulin preparations comprising anti-Aβ IgM according to the present invention can be a safer alternative when used for passive immunization of those suffering from, or at risk for the development of, amyloid-related disease.

The anti-amyloid peptide immunoglobulin preparations of the invention can be formulated in a pharmaceutical composition with a pharmaceutically acceptable carrier. The phrase "pharmaceutically acceptable" refers to molecular entities and compositions that are physiologically tolerable and do not typically produce an allergic or similar untoward reaction, such as gastric upset, dizziness and the like, when administered to a human. As used herein, the term "pharmaceutically acceptable" can mean approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

Pharmaceutical compositions comprising the anti-amyloid immunoglobulin preparations of the invention can be introduced parenterally, transmucosally, e.g., orally (per os), nasally, or rectally, or transdermally. Parenteral routes include intravenous, intra-arteriole, intramuscular, intradermal, subcutaneous, intraperitoneal, intraventricular, and intracranial administration. Administration can be directly into the cerebrospinal fluid, e.g., by a spinal tap.

In other embodiments, the preparations of the invention can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss: New York, pp. 353-365 (1989); Lopez-Berestein, ibid., pp. 317-327; see generally ibid.).

In yet another embodiment, the preparations of the invention can be delivered in a controlled release system. For example, a polypeptide can be administered using intravenous infusion with a continuous pump, in a polymer matrix such as poly-lactic/glutamic acid (PLGA), a pellet containing a mixture of cholesterol and the anti-amyloid peptide antibody compound (SILASTICR, Dow Corning, Midland, Mich.; see U.S. Pat. No. 5,554,601) implanted subcutaneously, an implantable osmotic pump, a transdermal patch, liposomes, or other modes of administration. In one embodiment, a pump can be used (see Langer (1990); Sefton, *CRC Crit. Ref Biomed. Eng.* 14:201 (1987); Buchwald et al., *Surgery* 88:507 (1980); Saudek et al., *N. Engl. J. Med.* 321:574 (1989)). In another embodiment, polymeric materials can be used (see Medical Applications of Controlled Release, Langer and Wise (eds.), CRC Press: Boca Raton, Fla. (1974); Controlled Drug Bioavailability, Drug Product Design and Performance, Smolen and Ball (eds.), Wiley: N.Y. (1984); Ranger and Peppas, *J. Macromol. Sci. Rev. Macromol. Chem.* 23:61 (1983); see also Levy et al., *Science* 228:190 (1985); During et al., *Ann. Neurol.* 25:351 (1989); Howard et al., *J. Neurosurg.* 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, vol. 2, pp. 115-138 (1984)). A controlled release device can be introduced into a subject in proximity of the site of amyloidosis. Controlled release systems are discussed in the review by Langer (*Science* 249: 1527-1533 (1990)).

The immunoglobulin preparations and methods of the invention are useful for treating neurological diseases or disorders associated with a deficiency of anti-amyloid antibodies. Thus, a disease or disorder subject to treatment or prevention according to the invention can be a neuropathy involving amyloid deposition, and can be associated with specific or general immunodeficiency. These diseases include, but are not limited to, AD; Kuru, Creuzdfelt-Jacob's disease, and other spongiform encephalopathies; Parkinson's Disease; and Huntington's chorea.

Dosage and Regimen

A constant in vivo supply of the anti-amyloid peptide antibodies from the immunoglobulin preparations of the invention can be ensured by providing a therapeutically effective dose (i.e., a dose effective to induce metabolic changes in a subject) at the necessary intervals, e.g., daily, every 12 hours, etc. These parameters will depend on the severity of the disease condition being treated, other actions, such as diet modifications that are implemented, the weight, age, and sex of the subject, and other criteria, which can be readily determined according to standard good medical practice by those of skill in the art. The anti-amyloid peptide immunoglobulin preparation is administered for at least ten days, at least 100 days, or for the life of the recipient.

The term "prevent" means to prophylactically interfere with a pathological mechanism that results in the disease or disorder, resulting in at least some clinically recognizable decrease in the rate of deterioration or ultimate extent of damage by the disease. In the context of the present invention, such a pathological mechanism can be an increase in processing of the amyloidogenic form of APP; dysregulation of Aβ clearance; or some combination of the two.

The term "treat" means to cause an improvement in a condition associated with the disease or disorder. In the context of the present invention, treatment includes a reduction in the level of Aβ, regulation of the formation of Aβ, decrease in aggregation of Aβ or the formation of amyloid plaques, or improvement of a cognitive defect in a subject suffering from a disease or disorder associated with amyloidosis, e.g., AD or an animal model of AD. A "therapeutically effective amount" of the immunoglobulin preparations of the invention can treat or prevent a clinically significant deficit in the activity, function, and response of the host. Alternatively, a therapeutically effective amount can be sufficient to cause a clinically significant improvement of a disease condition in the host.

A subject who "has an increased risk of developing" a neurological disease or disorder associated with amyloidosis can have a genetic predisposition to developing an amyloidosis, such as a person from a family that has members with familial AD (FAD). Alternatively, someone in his or her seventh or eighth decade is at greater risk for age-related AD.

A subject who "shows a symptom of" a neurological disease or disorder associated with amyloidosis presents with a symptom or complaint found in subjects who have or have had such a disease or disorder. For example, in AD, these symptoms can include development of dementia, memory defects, and the like in the fifth and sixth decade, as discussed above.

An "Aβ level reducing dose" is an amount of anti-amyloid peptide antibody that causes a decrease in the level of Aβ, e.g. in the brain or spinal fluid of a treated subject. Dosages can range from about 0.1 μg anti-amyloid peptide antibody per kg body weight (μg/kg) to about 100 mg/kg; 0.5 μg anti-amyloid peptide antibody per kg body weight (μg/kg) to about 50 mg/kg; or from about 5 μg/kg to about 10 mg/kg. The amount of anti-amyloid peptide antibody used to decrease the level of Aβ can be an amount corresponding to the level of anti-amyloid peptide antibody in a biological sample, especially blood (including plasma and serum) and cerebrospinal fluid (CSF), from a normal subject.

"Reducing a level of amyloid-β (Aβ) peptides" can refer to decreasing the amount of Aβ 1-42 in vivo. Aβ can accumulate in blood, cerebrospinal fluid, or organs. The primary organ of interest for reducing the level of Aβ is the brain, but Aβ levels can also be reduced in body fluids, tissues, and/or other organs by the practice of this invention.

Effective doses of the compositions of the present invention, for the treatment of the above described conditions vary depending upon many different factors, including means of administration, target site, physiological state of the patient, whether the patient is human or an animal, other medications administered, and whether treatment is prophylactic or therapeutic. Treatment dosages can be titrated to optimize safety and efficacy.

For passive immunization with an antibody or immunoglobulin preparation, the dosage ranges from about 0.0001 to 2000 mg/kg, 200 to 1000 mg/kg, and more usually 0.01 to 100 mg/kg, of the host body weight. For example, dosages can be 100 mg/kg body weight or 1000 mg/kg body weight or within the range of 100-1000 mg/kg. An exemplary treatment regime entails administration once per every two weeks or once a month or once every 3 to 6 months. Antibodies are usually administered on multiple occasions. Intervals between single dosages can be weekly, monthly or yearly. Intervals can also be irregular as indicated by measuring blood levels of antibody to Aβ in the patient. In some methods, dosage is adjusted to achieve a plasma antibody concentration of 1-50 mg/ml, and in some methods 1-20 mg/ml. Alternatively, antibodies can be administered as a sustained release formulation, in which case less frequent administration is required. Dosage and frequency vary depending on the half-life of the antibodies in the patient.

The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Agents of the invention can optionally be administered in combination with other agents that are at least partly effective in treatment of amyloidogenic disease. In the case of AD and Down's syndrome, in which amyloid deposits occur in the brain, agents of the invention can also be administered in conjunction with other agents that increase passage of the agents of the invention across the blood-brain barrier.

Passive Immunization

In general, the procedures for monitoring passive immunization are similar to those that can be used for monitoring active immunization. However, the antibody profile following passive immunization typically shows an immediate peak in antibody concentration followed by an exponential decay. Without a further dosage, the decay approaches pretreatment levels within a period of days to months depending on the half-life of the antibody administered. For example the half-life of some human antibodies is of the order of 20 days.

In some methods, a baseline measurement of antibody to Aβ in the patient can be made before administration, a second measurement can be made soon thereafter to determine the peak antibody level, and one or more further measurements are made at intervals to monitor decay of antibody levels. When the level of antibody has declined to baseline or a predetermined percentage of the peak less baseline (e.g., 50%, 25% or 10%), a further dosage of antibody is administered. In some methods, peak or subsequent measured levels less background can be compared with reference levels previously determined to constitute a beneficial prophylactic or therapeutic treatment regime in other patients. If the measured antibody level is significantly less than a reference level (e.g., less than the mean minus one standard deviation of the reference value in population of patients benefiting from treatment), administration of an additional dosage of antibody can be indicated.

EXAMPLES

The following examples are illustrative of the methods and compositions of the invention, and are not intended as limiting of the scope of the invention as claimed.

Example 1

Preparation of IgM and IgM Fragments

To summarize, IgM was purified from the ANX column eluate from the IGIV preparation process (the second anion exchange step of the process as disclosed in U.S. Pat. No. 6,307,028 to Lebing, et al. (Lebing, et al.), the contents of which are fully incorporated herein by reference), followed by gel filtration on SUPEROSE 6 which yields greater than 90% pure IgM. The major impurities are IgA (~6-8%) and IgG (<2%). In order to remove isoagglutinins, IgM was passed through a column containing immobilized synthetic antigen A and B. Details are provided below.

Preparation of Highly Purified, Low-Isoagglutinin, Low-Oligomer Human IgM was achieved by size exclusion chromatography of IGIV anion-exchange eluate (ANX eluate) followed by isoagglutinin removal by affinity chromatography. The target profile for the IgM preparation was defined to include limits of less than 5% IgA, less than 5% oligomeric IgM, and less than 0.3 EU/ml endotoxin. The European Pharmacopoeia (EP) limit for isoagglutinin activity was applied to IgM: less than 1:64 at 50 mg/ml.

All buffers were autoclaved and filtered through a 0.22 μm filter into sterile, pyrogen-free bags prior to use. The starting material, ANX eluate, is a pH 5.1, 0.5M acetate, 0.2% protein solution which can contain as much as 50% IgM. The non-IgM protein material present in ANX eluate is mostly IgG and IgA. 1.3 L of frozen ANX column eluate was thawed and the pH adjusted to 7.95 with 1.0 N NaOH. After filtration through a sterile 0.22 μm filter, the material was concentrated on a 100 K PELLICON mini and/or a PELLICON XL cassette (Millipore Corporation, Bedford, Mass.) to 15 to 25 mg/ml. 65 ml of the concentrate (approximately 1150 mg of protein) was loaded onto a 5.0 cm×70 cm SUPEROSE 6 FF Prep grade column (Pharmacia, Upsala, Sweden) equilibrated with TBS at a linear flow rate of 15.3 cm/hr. During elution of the IgM fraction, a 5.0 cm×5.1 cm Atri/Btri PAA SEPHAROSE 6 FF column (GlycoTech Corporation, Rockville, Md.) was plumbed in series.

Figure 9:
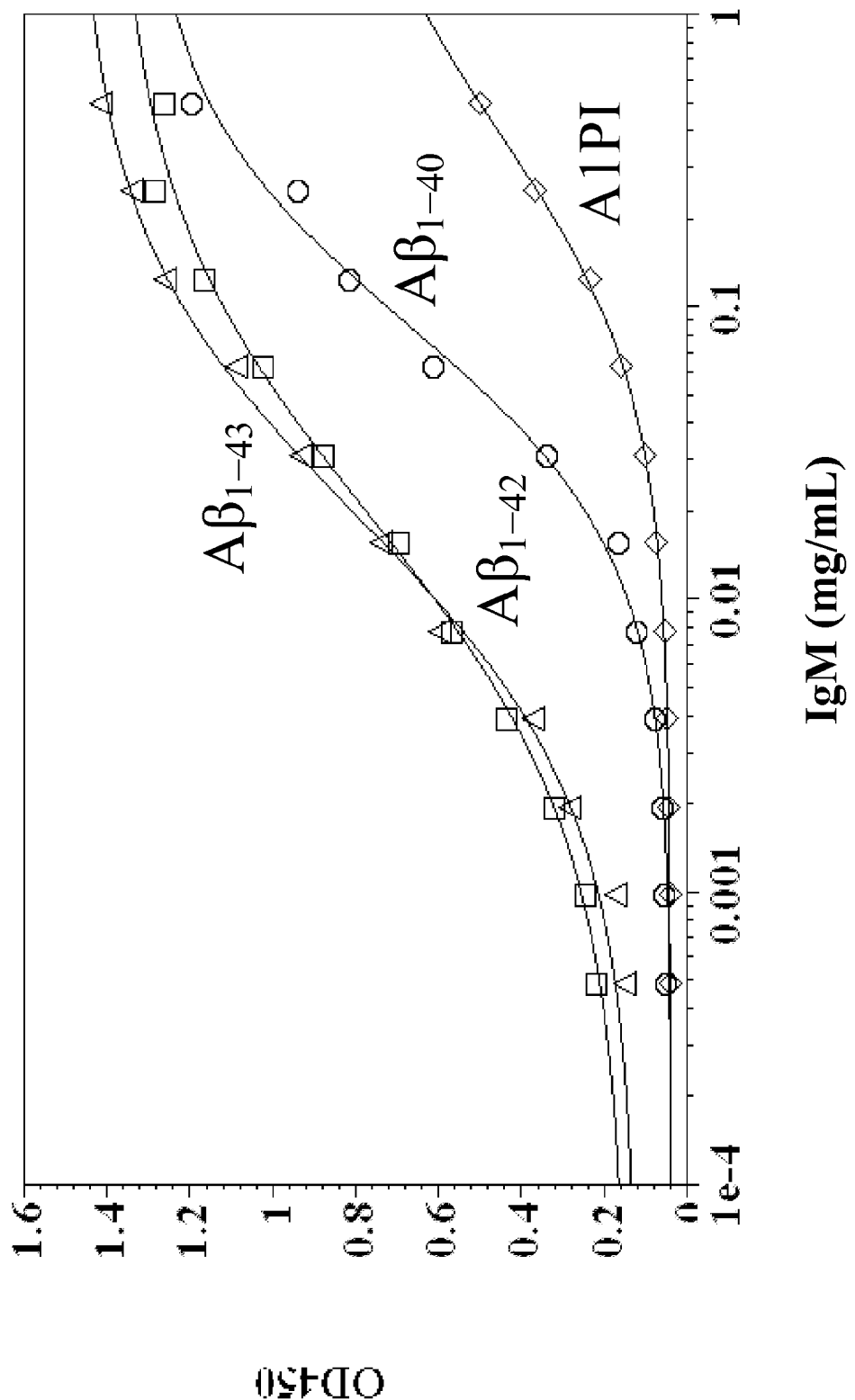
FIG. 9 is a graph illustrating binding of IgM to Aβ 1-40, Aβ 1-42, Aβ 1-43, and α1PI coated plates.

As seen in FIG. 9, the central portion of the IgM peak (approximately 200 ml) was collected into sterile containers, sampled and immediately dialyzed against 0.2M glycine, pH 4.2, using sterile dialysis tubing. The dialysis consisted of four ×2 L changes over a period of 18 hrs at 4° C. Following dialysis, the sublots were sterile filtered and diluted to 2.0 mg/ml, then stored at +4° C. until bulking. Percent yields for each sublot were between 27 and 68% recovery of IgM. The majority of the IgM losses were due to oligomerization of IgM, which eluted in the void volume of the size-exclusion column.

Eleven sublots of material were bulked to form the single lot of IgM, which was then sterile filtered through a 0.22 μm filter and filled into four 280-ml sterile vials and twenty 1-ml vials. Formulation of the material into 0.2 M glycine buffer, pH 4.2, yielded a product which was shown to be stable against oligomerization at +4° C. for 12 months. Biochemical characterization of the material is described in Table 2.4.1.

TABLE 1

Characterization of Purified IgM.

| Test | Method | Specification | Assay Results |
|---|---|---|---|
| Total Protein | A280/ml | 1.5-2.5 mg/ml | 1.6 mg/ml |
| % Oligomer | SEC-HPLC | NMT 5% | <1.0% |
| % IgA | Immunonephelometry | NMT 5% | 1.6% |
| IgG | Immunonephelometry | | 0.03 mg/ml |
| IgM | Immunonephelometry | | 2.51 mg/ml |
| CH50 | 100 $CH_{50}$ | <75 units | 43 |
| Isoagglutinin | Isoagglutination Cross Match Test | Negative at 1:64 at 50 mg/ml | Negative at 1:4 |
| Endotoxin | LAL | <0.3 EU/ml | <0.06 EU/ml |
| pH | Undiluted | 4.0-4.4 | 4.24 |
| Purity | Reduced SDS-PAGE Gel | | 91% |
| % Protein | Biuret | 1-2 mg/ml | 2.20 mg/ml |

Total protein was calculated using the published specific ($\epsilon^{1\%}_{280}$) extinction coefficient of 13.3. Amino acid analysis (Commonwealth Biotechnologies, Richmond, Va.) of this IgM preparation yielded a specific extinction coefficient of 13.4. Percent Oligomer was determined using a 10/30 SUPEROSE 6 PHARMACIA HR column and is defined as the percent area at 15.7 minutes divided by the total area of the chromatogram. Samples submitted for Isoagglutination Cross Match Test were concentrated to 50 mg/ml after pH adjustment to 7.5 with 10×PBS. Purity by Reduced SDS-PAGE is defined by a two-step procedure. First, the content of the only unidentified X-band on the gel is determined; it gives the total percentage of immunoglobulins in the preparation. In the second step, the content of IgA and IgG is determined by measuring the intensity of the heavy chain bands of all three immunoglobulins. Thus, the purity of IgM is equal to 100%-% Xband-% IgA-% IgG.

It was found that IgM tends to form stable oligomers in a time- and concentration-dependent process. The purification strategy, therefore, included steps to minimize IgM oligomerization such as processing at low pH, keeping the IgM preparations at low concentration, and minimizing IgM exposure to high salt. The final preparations of IgM were formulated in a 0.2 M Glycine (pH 4.2) solution to avoid oligomer formation; in this formulation IgM is stable and suitable for injections.

Figure 7:
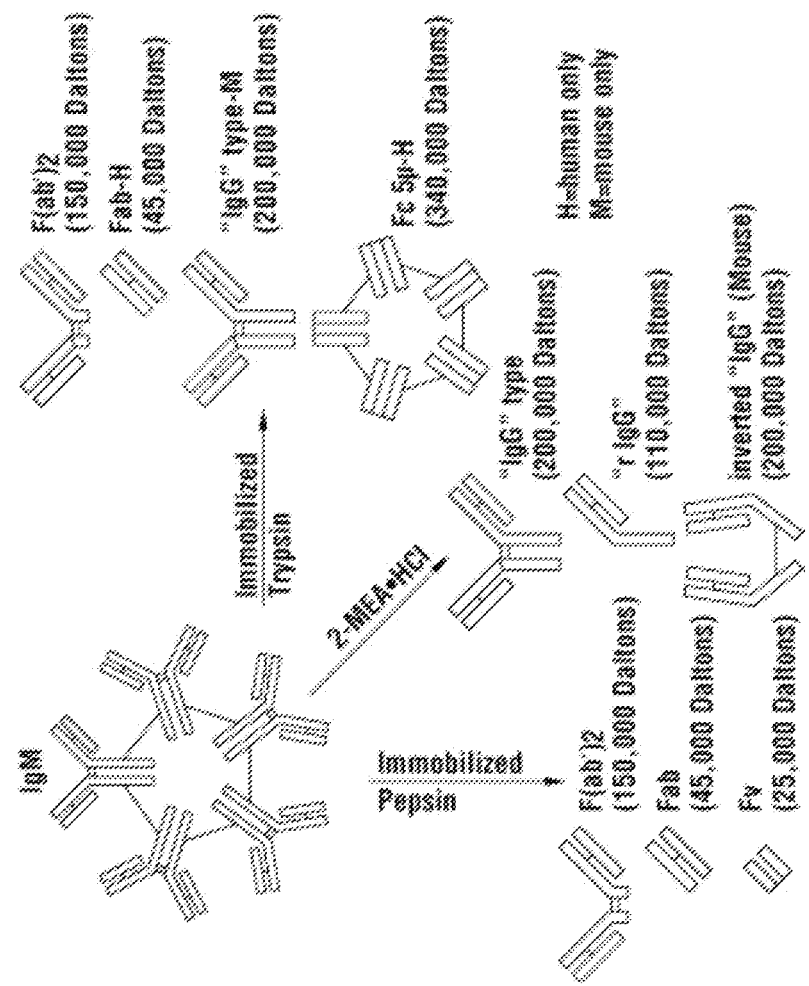
FIG. 7 is a photograph showing the results of gel electrophoresis of 2-mercaptoethylamine (MEA)-fragmented IgM.
Figure 6:
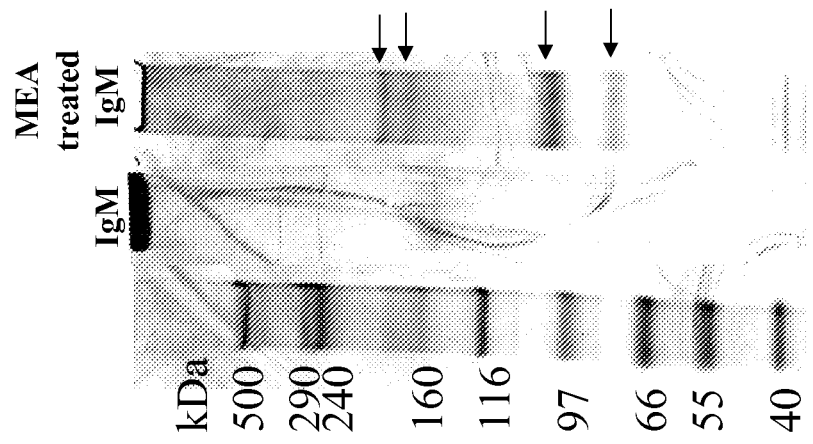
FIG. 6 is a schematic drawing illustrating IgM fragmentation methods.

For experiments involving IgM fragments, such fragments were prepared using a commercially available IgM fragmentation kit (Pierce Cat. No. 44887). This kit has the ability to fragment IgM by three methods (See FIG. 6). Alkylation and reduction of IgM with 2-mercaptoethylamine and iodoacetamide was used to generate IgM derivatives of interest. Derived IgMs were analyzed on a 3-8% Tris-Acetate PAGE (See FIG. 7). Four main IgM fragments corresponding to the expected molecular weights for monomeric IgM (~200 KDa) and half of the monomeric IgM (~100 KDa) were noted. The fragments generated during a 2-mercaptoethylamine (MEA) treatment of IgM were compared to untreated IgM on a 3-8% Tris-Acetate gel run for 90 minutes at 150 volts. The gel was Coomassie stained and scanned using the QUANTITY ONE software. FIG. 6 illustrates the results of the MEA IgM fragmentation process, along with results using other methods. FIG. 7 shows the results of gel electrophoresis of IgM and MEA-treated IgM (showing fragment species corresponding to "IgG"-type and "r IgG" fragments illustrated in FIG. 6).

Examples 2-10

Binding Assays

In Examples 2-10 below, following the indicated experiments, plates were washed 6 times with wash buffer (Tris-Buffered-Saline with 0.1% polyoxyethylene sobritan monolaurate and 0.01% sodium azide). 100 µl of a horseradish peroxidase-conjugated, goat anti-human IgM (with specificity to the Fc5µ region) was added to each well, and the plate was incubated for 1 hour at 25° C. with gentle shaking. The plate was then washed 3 times with wash buffer and developed with 100 ul of TMB microwell peroxidase substrate (KPL cat#50-76-00) for 5 minutes at room temperature. The reaction was then stopped using 100 ul of 1M phosphoric acid and the plate was read at 450 nm on a SPECTRAMAX 190 plate reader with computer interface using SOFTMAX PRO4.0 software.

Example 2

IgM Binding to Full-Size Aβ 1-42, Aβ 22-35, and α1-Protein Inhibitor

Figure 2:
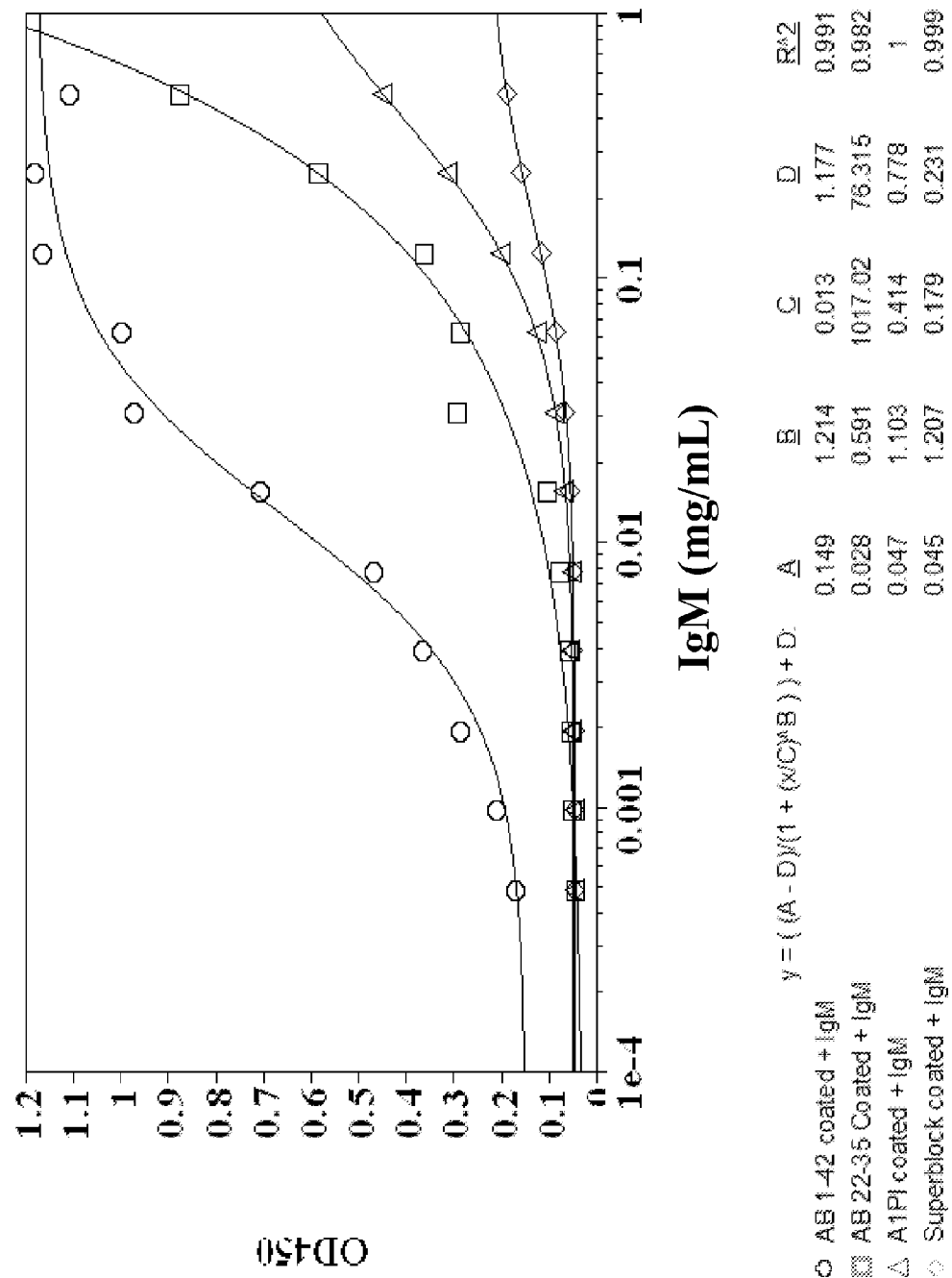
FIG. 2 is a graph illustrating IgM binding to Aβ 1-42, Aβ 22-35, α-1 protease inhibitor (α1PI) and SUPERBLOCK-coated wells.

A 96-well Nunc MAXISORP microtiter plate was passively coated with 100 µl of 2 ug/ml Aβ 1-42, Aβ 22-35, and an unrelated protein (α-1 protease inhibitor, α1PI) for 1 hour at 25° C. with gentle shaking. The last two rows in the plate were coated with 100 ul of PIERCE SUPERBLOCK to serve as a negative (non-specific) control. Following the coating procedure, the plate was washed twice with 300 µl of wash buffer. The plate was blocked with 100 µl of SUPERBLOCK for 1 hour at 25° C. with gentle shaking and washed twice with wash buffer. 100 µl of IgM serially diluted in SUPERBLOCK was added to the plate and incubated for 2 hours at 25° C. with gentle shaking. The results are shown in FIG. 2.

Example 3

Immunodepletion of IgM by Aβ 1-42

Figure 3:
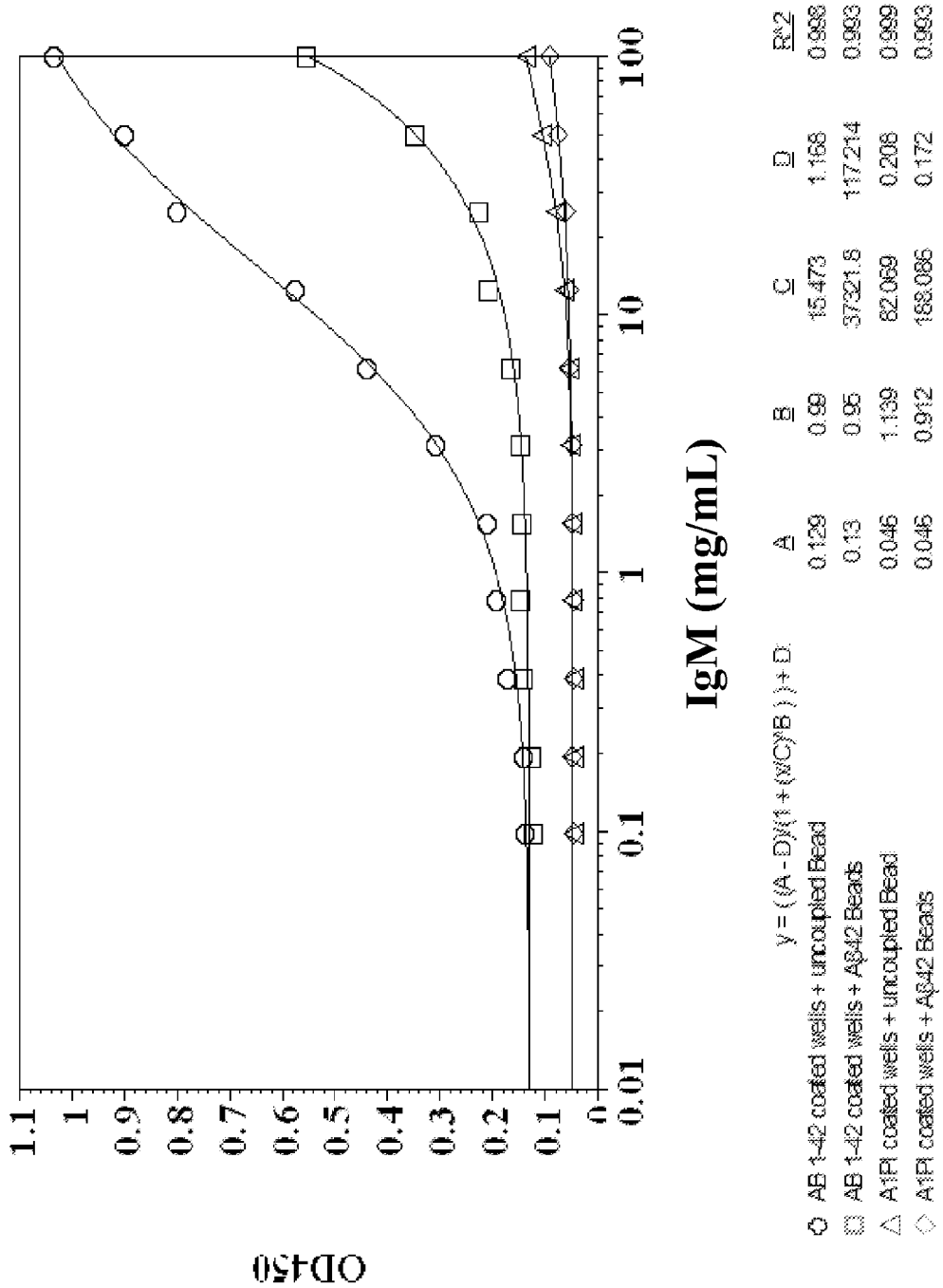
FIG. 3 is a graph illustrating immunodepletion of IgM by Aβ 1-42 coupled beads tested on plate coated with Aβ 1-42 and α1PI.

A 96-well NUNC MAXISORP microtiter plate was passively coated with 100 µl of 2 µg/ml Aβ 1-42 and α1PI for 1 hour at 25° C. with gentle shaking. Following the coating procedure, the plate was washed twice with wash buffer. The plate was blocked with 100 µl SUPERBLOCK for 1 hour at 25° C. with gentle shaking and washed twice with wash buffer. Previously 0.2 milligrams of IgM was incubated with an uncoupled and Aβ 1-42 coupled affinity purification column overnight at 4° C. with gentle rocking. The depleted IgM material (flowthrough) was serial diluted in SUPERBLOCK and incubated for 2 hours at 25° C. with gentle shaking. The results are shown in FIG. 3.

Example 4

Inhibition of IgM Binding to Aβ by Aβ-Related and Unrelated Peptides

Two 96-well NUNC MAXISORP microtiter plates were passively coated with 100 µl of 2 µg/ml Aβ 1-42 for 1 hour at 25° C. with gentle shaking. Following the coating procedure, the plates were washed twice with wash buffer. The plates were blocked with 100 µl of SUPERBLOCK for 1 hour at 25° C. with gentle shaking and washed twice with wash buffer. 100 µl of Aβ peptides (Aβ 1-28, Aβ 22-35, Aβ 25-35, Aβ 1-40, and Aβ 1-42) and α1PI were serial diluted in SUPERBLOCK with 0.1 mg/ml IgM, added to the plates and incubated for 2 hours at 25° C. with gentle shaking. Also, 100 µl of IgM, serial diluted in SUPERBLOCK, was added to the top two rows of each plate. The results are shown in FIGS. 4A and 4B.

Example 5

Inhibition of IgM Binding to Aβ 1-42 by Competing GAMUNEX

A 96-well NUNC MAXISORP microtiter plate was passively coated with 100 µl of 2 ug/ml Aβ 1-42 for 1 hour at 25° C. with gentle shaking. Following the coating procedure, the plate was washed twice with wash buffer. The plate was blocked with 100 µl of SUPERBLOCK for 1 hour at 25° C. with gentle shaking and washed twice with wash buffer. 100 µl of GAMUNEX serial diluted in SUPERBLOCK with 0.1 mg/ml IgM was added to the plate and incubated for 2 hours at 25° C. with gentle shaking. Also 100 µl of IgM and GAMUNEX, serial diluted in SUPERBLOCK, were added to the plate and served as positive and negative controls. The results are shown in FIG. 5.

Example 6

Aβ 1-42 Binding by MEA-Fragmented IgM

Figure 8:
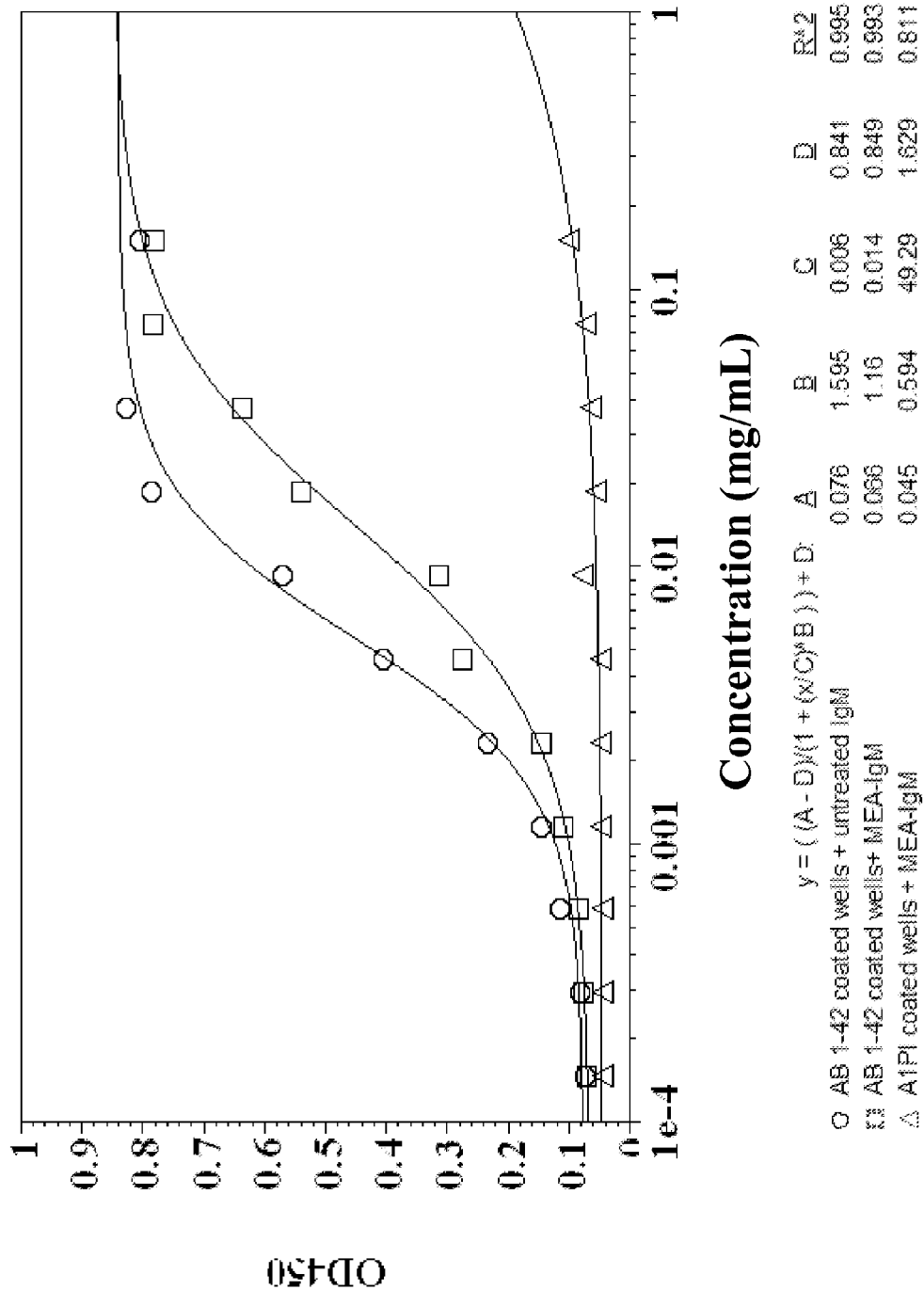
FIG. 8 is a graph illustrating binding of MEA-fragmented IgM to Aβ 1-42 coated wells.

A 96-well NUNC MAXISORP microtiter plate was passively coated with 100 µl of 2 µg/ml Aβ 1-42 and α1PI for 1 hour at 25° C. with gentle shaking. Following the coating procedure, the plate was washed twice with wash buffer. The plate was blocked with 100 µl of SUPERBLOCK for 1 hour at 25° C. with gentle shaking and washed twice with wash buffer. 100 µl of IgM and 2-mercaptoethylamine treated IgM, serial diluted in SUPERBLOCK, was added to the plate and incubated for 2 hours at 25° C. with gentle shaking. The results are shown in FIG. 8.

Example 7

IgM binding to Aβ 1-40, Aβ 1-42, Aβ 1-43 and α1PI Coated Plates

A 96-well NUNC MAXISORP microtiter plate was passively coated with 100 µl of 2 µg/ml Aβ 1-40, Aβ 1-42, Aβ 1-43 and α1PI (negative control) for 1 hour at 25° C. with gentle shaking. Following the coating procedure, the plate was washed twice with wash buffer. The plate was blocked with 100 µl of SUPERBLOCK for 1 hour at 25° C. with gentle shaking and washed twice with wash buffer. 100 µl of IgM serially diluted in SUPERBLOCK was added to plate and incubated for 2 hours at 25° C. with gentle shaking.

In the IgM pool, very similar titer of specific binding activity for Aβ 1-42 and Aβ 1-43 was demonstrated. This titer is about 10 times higher than the titer for Aβ 1-40. The data demonstrate that the majority of the anti-Aβ titer in the IgM pool is directed to the extreme C-terminal end of Aβ. Therefore, it appears as though amino acids 41 and 42 seem to be required for binding to IgM. See FIG. 9.

Example 8

IgM Binding to Aβ 1-40, Aβ 1-42, Aβ 1-43 and α1PI Coated Plates

A 96-well NUNC MAXISORP microtiter plate was passively coated with 100 µl of 2 µg/ml Aβ 1-42 for 1 hour at 25° C. with gentle shaking. Following the coating procedure, the plate was washed twice with wash buffer. The plate was blocked with 100 µl of SUPERBLOCK for 1 hour at 25° C. with gentle shaking and washed twice with wash buffer. 0.1 mg/ml solutions of Aβ 1-40, Aβ 1-42 and Aβ 1-43 were each spiked with 7 mg/ml IgM to obtain a 0.07 mg/ml IgM final concentration. Next, the solutions were serially diluted in 0.07 mg/ml IgM and 100 µl was added to plate and incubated for 2 hours at 25° C. with gentle shaking. The plate was then washed 6 times with wash buffer. 100 µl of horseradish peroxidase conjugated goat anti-human IgM was added to each well and the plate was incubated for 1 hour at 25° C. with gentle shaking.

Figure 10:
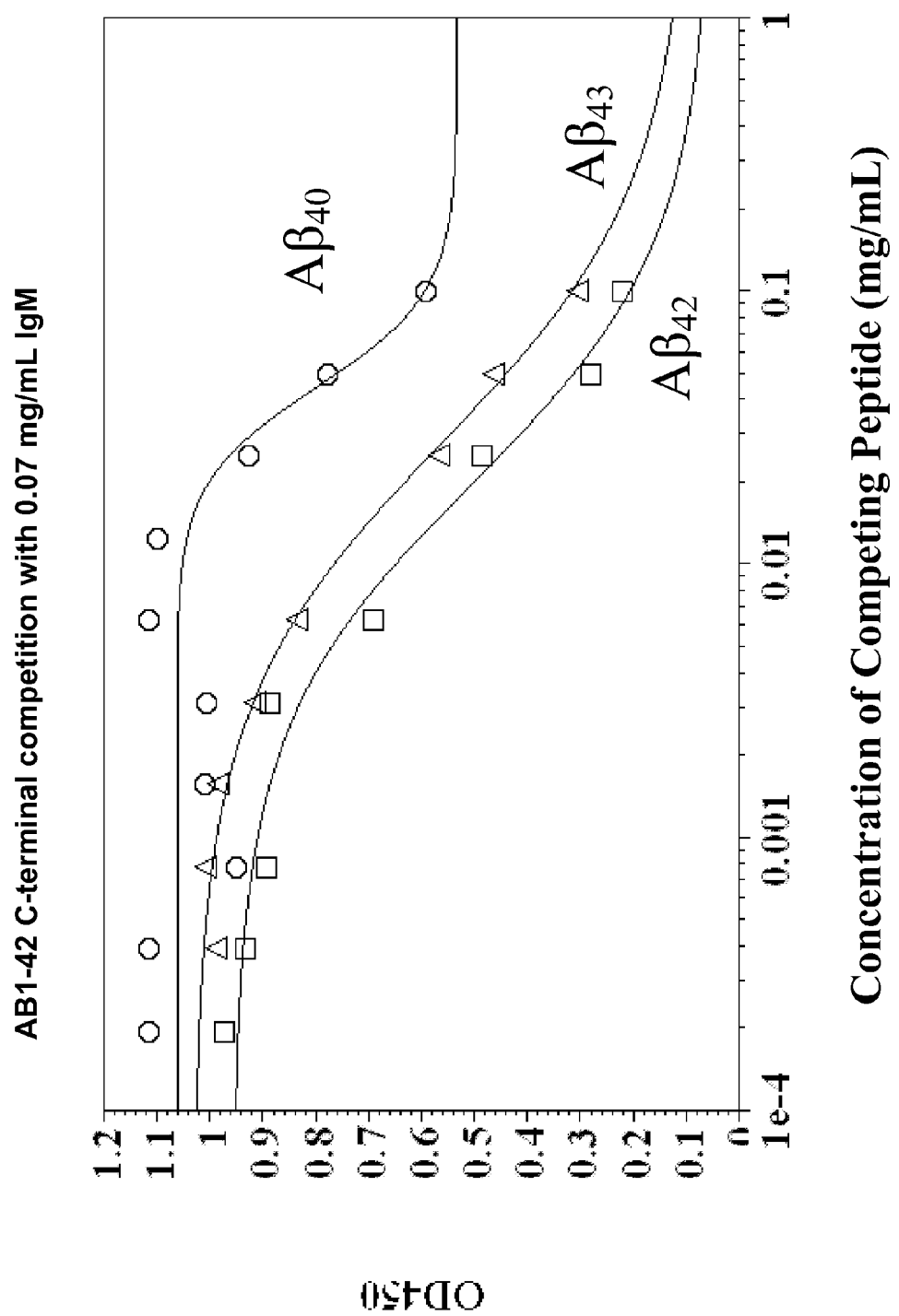
FIG. 10 is a graph illustrating binding of IgM to Aβ 1-42 coated plates in the presence of competing Aβ 1-40, Aβ 1-42, and Aβ 1-43.

The data demonstrate that Aβ 1-42 and Aβ 1-43 completely inhibit IgM binding to Aβ 1-42 coated plates. Aβ 1-40, even at concentrations 10 times more than Aβ 1-42 and Aβ 1-43, only inhibits about 50% of IgM binding to Aβ 1-42 coated plates. This experiment again points to the importance of the extreme C-terminal end of amyloid β (amino acids 41 and 42) for binding to IgM. See FIG. 10.

Example 9

Aβ 1-42 Binding—Competing Aβ 1-40, Aβ 1-42, Aβ 33-42, and Aβ 37-42

A 96-well NUNC MAXISORP microtiter plate was passively coated with 100 ul of 2 ug/ml Aβ 1-42 for 1 hour at 25° C. with gentle shaking. Following the coating procedure, the plate was washed twice with wash buffer. The plate was blocked with 100 µl of SUPERBLOCK for 1 hour at 25° C. with gentle shaking and washed twice with wash buffer. A 0.5 mg/ml solution of Aβ 37-42 and 0.1 mg/ml solutions of Aβ 1-40, Aβ 1-42 and Aβ 33-42 were each spiked with 7 mg/ml IgM to obtain a 0.07 mg/ml IgM final concentration. Next the solutions were serially diluted in 0.07 mg/ml IgM and 100 ul was added to plate and incubated for 2 hours at 25° C. with gentle shaking.

Figure 11:
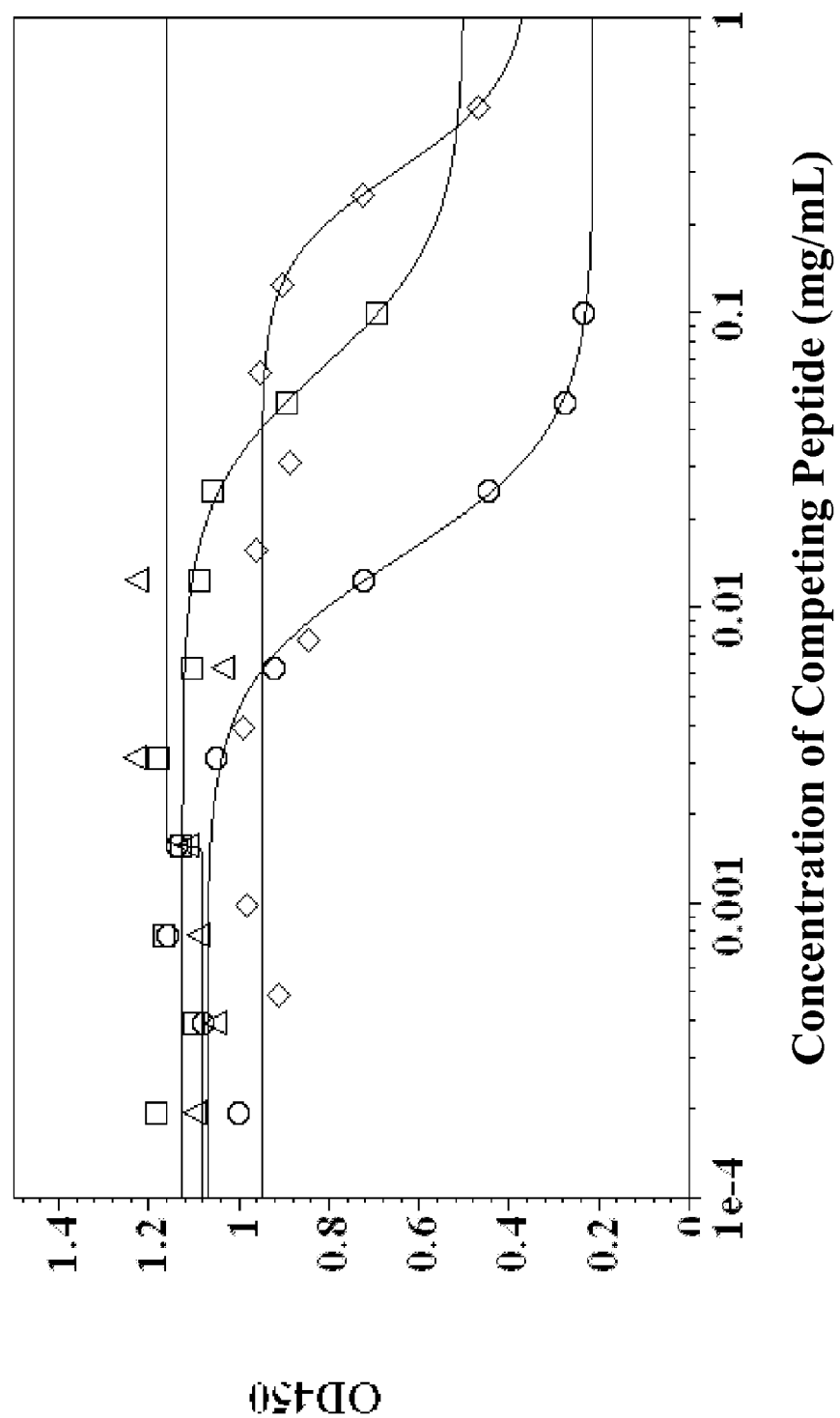
FIG. 11 is a graph illustrating binding of IgM to Aβ 1-42 coated plates in the presence of competing Aβ 1-40, Aβ 1-42, Aβ 33-42, and Aβ 37-42.

Aβ 1-42 is able to completely inhibit IgM binding to Aβ 1-42 coated plates. The fragmented amyloid β peptides show no more inhibition than Aβ 1-40. This data demonstrates that in addition to amino acids 41 and 42 there appears to be a need for a peptide greater than 10 amino acids with possibly a tertiary structure to inhibit IgM binding to Aβ 1-42 coated plates. See FIG. 11.

Example 10

Aβ 1-42 Binding—Competing Aβ 1-42 and Scrambled Aβ 1-42

A 96-well NUNC MAXISORP microtiter plate was passively coated with 100 µl of 2 µg/ml Aβ 1-42 for 1 hour at 25° C. with gentle shaking. Following the coating procedure, the plate was washed twice with wash buffer. The plate was blocked with 100 µl of SUPERBLOCK for 1 hour at 25° C. with gentle shaking and washed twice with wash buffer. 0.1 mg/ml solutions of Aβ 1-42 and scrambled Aβ 1-42 were each spiked with 7 mg/ml IgM to obtain a 0.07 mg/ml IgM final concentration. Next the solutions were serially diluted in 0.07 mg/ml IgM and 100 µl was added to plate and incubated for 2 hours at 25° C. with gentle shaking.

Figure 12:
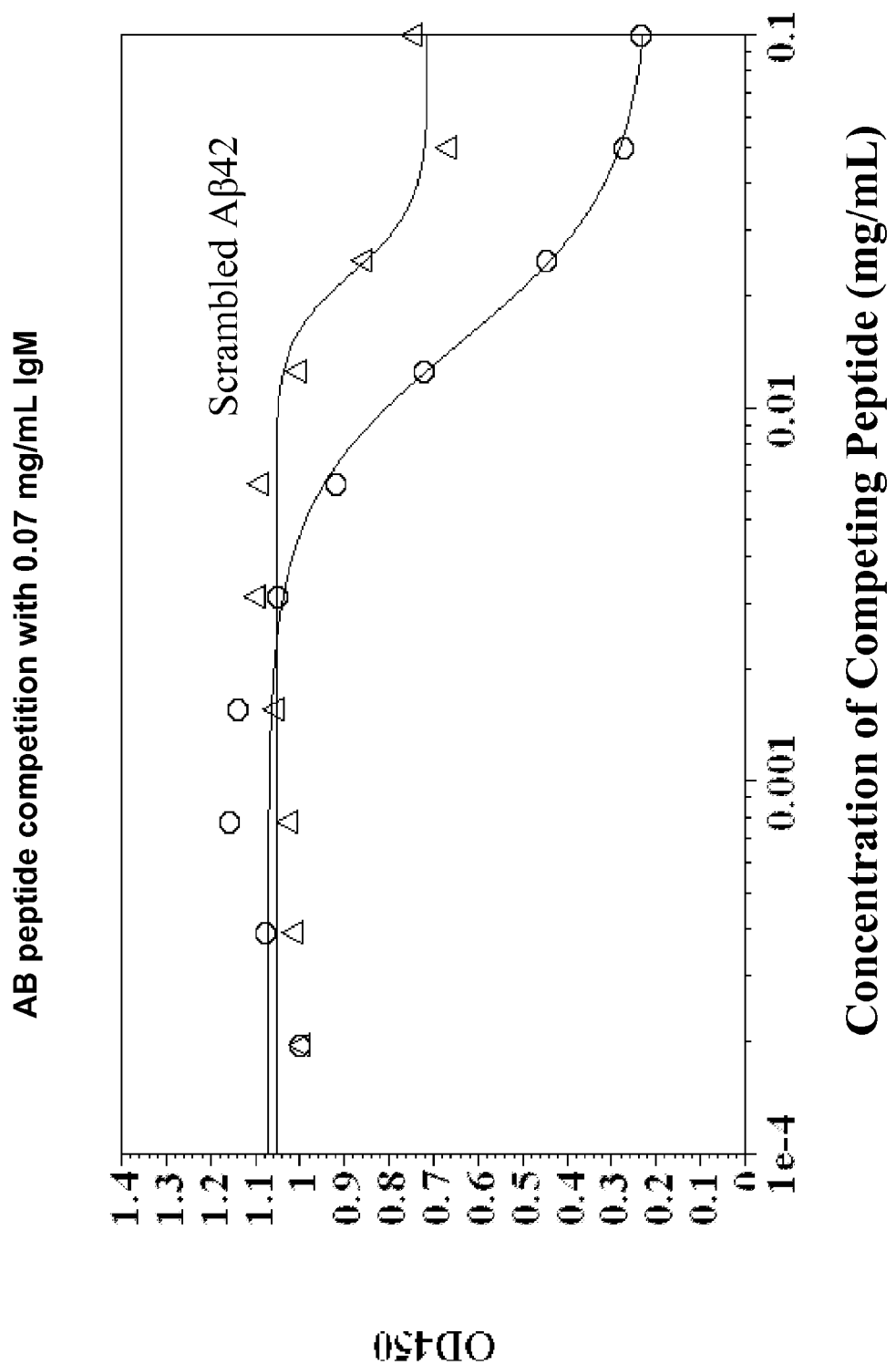
FIG. 12 is a graph illustrating binding of IgM to Aβ 1-42 coated plates in the presence of competing Aβ 1-42 and scrambled Aβ 1-42.
Figure 13:
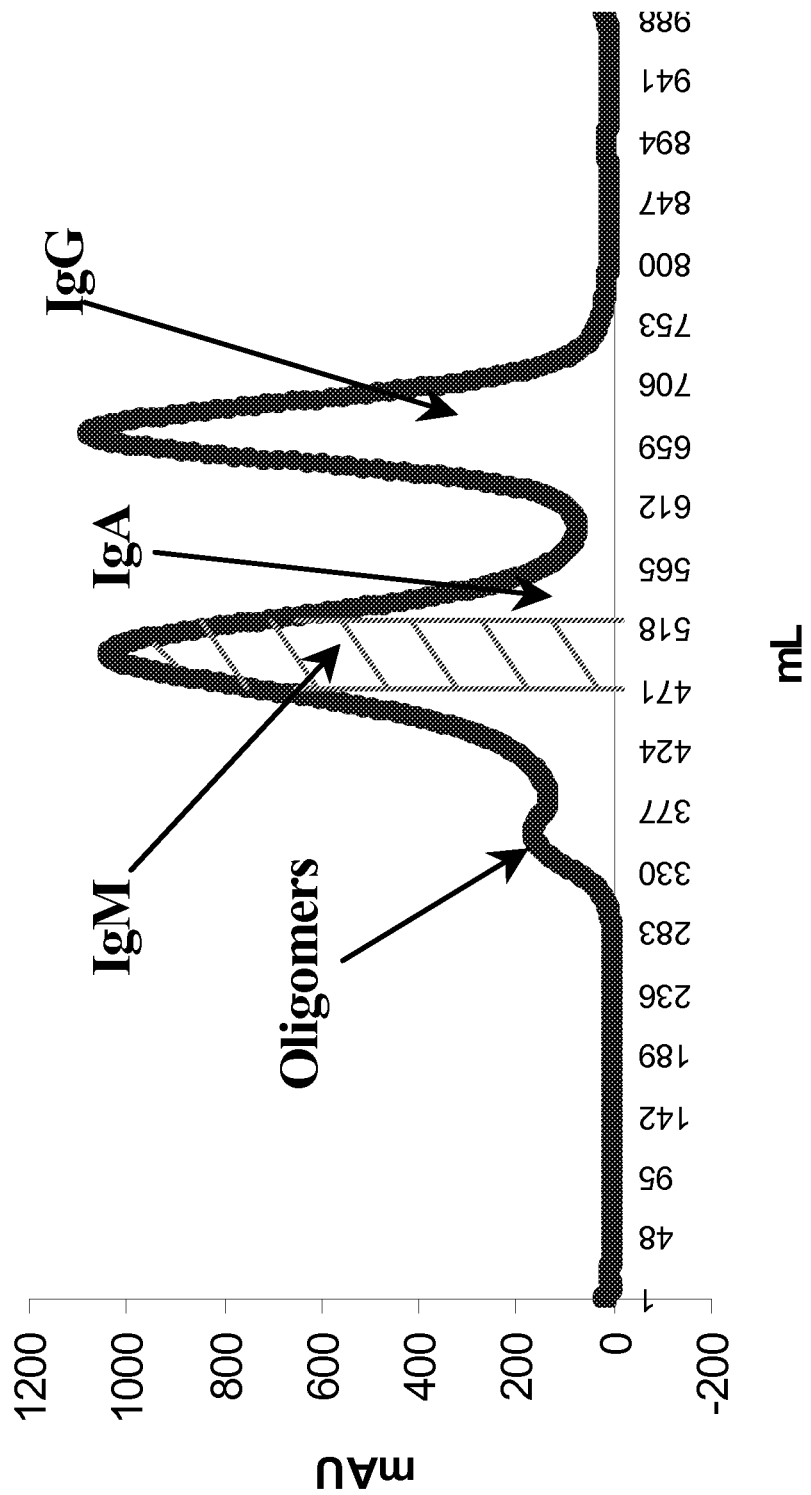
FIG. 13 is a graph illustrating a chromatographic profile of an IgM preparation of the invention.

Data demonstrates the specificity of the IgM titer is to Aβ 1-42 and not to peptide of the same size containing all 42 amino acids. See FIG. 12.

Example 11

IgM, Monomeric IgM, and IgG Binding to Aβ 1-42

The OCTET system (ForteBio, Inc., Menlo Park, Calif.) utilizes Bio-Layer Interferometry (BLI) to measure concentration, affinity and kinetics between two proteins/peptides. BLI detects changes in the interference pattern (reflected light) as the number of molecules increases or decreases from the tip of the detector.

Streptavidin-coated biosensors were first placed in wells containing PBS to equilibrate the detectors. Next, the biosensors were placed in wells containing 2 µg/ml biotinylated Aβ 1-42 and then moved to wells containing PBS so that a background interference profile could be created. These biosensors were then moved to wells that contained either IgM pool, monomeric IgM pool, or IgG pool (GAMUNEX) and the association rates were determined. Finally, the biosensors were moved to wells containing PBS to measure the dissociation rates.

Data generated based on this experiment demonstrated that the IgM pool and the monomeric IgM pool have at least a 5-fold higher affinity to biotinylated Aβ 1-42 than the IgG pool. (GAMUNEX).

Example 12

Transgenic Mouse AD Model

The B6; SJL-Tg(APPSWE)2576 Kha or "Tg2576" mouse expresses a mutated form of the human APP695 gene driven by a hamster prion protein gene promoter (see U.S. Pat. No. 5,877,399). These mice have normal spatial reference memory at three months of age but show impairment by 9 to 10 months of age (Hsiao, et al., "Correlative memory deficits, Aβ elevation, and amyloid plaques in transgenic mice," *Science* 274:99-102 (1996)). Brain transgenic APP content is 5.6 times more than endogenous APP. This increase accompanies the appearance of certain behavioral deficits. Numerous Congo Red-positive Aβ plaques are present with elevated levels of soluble Aβ. Amyloid plaques appear to stimulate a cellular inflammatory response. Both hypertrophic astrocytes and activated microglia surround the plaques (Irizarry, M., "APP$_{sw}$ transgenic mice develop age-related Aβ deposits and neuropil abnormalities, but no neuronal loss in CA1," *J. Neuropathol. Exp. Neurol.* 56:965-73 (1997); Frautschy, S. A., et al., "The microglial response to amyloid plaques in APPsw transgenic mice," *Am. J. Pathol.* 152: 307-17 (1998)), and amyloid angiopathy appears in some vessels (Klunk, W., et al., "Staining of AD and Tg2576 mouse brain with X-34, a highly fluorescent derivative of chrysamine G and a potential in vivo probe for b-sheet fibrils," *Soc. Neurosci. Abstr* 23:1638 (1997)). In addition, key markers of oxidative stress are induced in Tg2576 mouse brain (Pappolla, M. A., et al., "Evidence of oxidative stress and in vivo neurotoxicity of β-amyloid in a transgenic mouse model of Alzheimer's disease," *Am. J. Pathol.* 152:871-7 (1998)), similar to what is seen in the brain of AD patients at autopsy.

Typically, 14 pregnant (10-15 day of gestation) Tg2576 and 4 pregnant wild-type females are received (Taconic Farms, Inc., Germantown, N.Y.). Mice (pups) are randomly assigned to treatment groups as follows (Table 2).

TABLE 2

Approximate numbers of mice per treatment.

| Strain | #/treatment | Saline | hIgM |
|---|---|---|---|
| Tg2576 | 26 | 8 | 32 |
| Wild-type | 8 | 8 | 8 |

Within 24 hours of birth, treated pups receive intraperitoneal injections of either sterile, normal saline (50 μl) or human IgM (hIgM) (50 μl of 20 μg/μl). Thereafter, mice are injected with either saline or hIgM according to the following schedule (Table 3—See Khole, V., et al., "Identification of epididymis specific antigen by neonatal tolerization," *Am. J. Repro. Immunol.* 44:350-356 (2000)).

TABLE 3

Neonatal Tolerization Immunization Schedule

| | Day 1 | Day 5 | Day 21 | Day 35 | Day 49 |
|---|---|---|---|---|---|
| Route[c] | i.p. | i.p. | s.q. | s.q. | s.q. |
| Concentration | 20 μg/μl | 20 μg/μl | 100 μg/μl | 100 μg/μl | 100 μg/μl |

TABLE 3-continued

Neonatal Tolerization Immunization Schedule

| | Day 1 | Day 5 | Day 21 | Day 35 | Day 49 |
|---|---|---|---|---|---|
| Volume | 50 μl | 50 μl | 100 μl[a] | 100 μl[a] | 100 μl[a] |
| Adjuvant[b] | No | No | Yes | Yes | Yes |

[a]Multiple sites.
[b]TITERMAX ® Gold (CytRx Corporation, Parkway Technology Park, Georgia).
[c]Injections will be made with a 27G, ½" needle.

The half-life of human polyreactive IgM (hIgM) in mice is 8.0 hours (Sigounas, G., et al., "Half-life of polyreactive antibodies," *J. Clin. Immunol.*, 14:134-140 (1994)). Thus, these antibodies are cleared from the circulation after 56 hours (7 half-lives). Beginning at 6 months of age, mice receive 100 μl (400 mg/kg) of hIgM without adjuvant, subcutaneously, on Tuesday and Friday of each week (Dodel, R. C., et al., "Intravenous immunoglobulins containing antibodies against β-amyloid for the treatment of Alzheimer's disease," *J. Neurol. Neurosurg. Psychiatry* 75: 1472-4 (2004)). Antibody treatment continues until termination of the study.

Mice are sampled on day 56 for antibodies to hIgM. Not more than 50 μl whole blood is obtained by nicking the lateral saphenous vein superficially with a sterile #15 scalpel blade. Manual pressure is applied to achieve hemostasis before mice are returned to cages. The sample is centrifuged at room temperature to separate blood cells from plasma. Plasma is harvested and immediately frozen at −80° C. until analysis.

Mice are humanely sacrificed using $CO_2$ gas at 12-15 months of age, or if they appear moribund prior to that time. Blood is obtained via the caudal vena cava following euthanasia. Brains are harvested, and half are flash frozen for analysis of soluble Aβ-peptide and half are placed in 10% neutral buffered formalin for immunohistochemial staining and histopathologic analysis. Stained plaques will be counted and soluble Aβ-peptide will be quantified in brain and plasma. Data will be examined for normality and equal variance. A t-test will be used to assess differences between treated and untreated mice. Groups will be considered different if the P-value <0.05.

From the foregoing it will be apparent that the invention provides for a number of uses. For example, the invention provides for the use of any of the Aβ-binding immunoglobulin preparations described herein in the treatment or prophylaxis of amyloidogenic disease, or in the manufacture of a medicament for use in the same.

The invention claimed is:

1. A method for preparing an immunoglobulin preparation comprising immunoglobulin M (IgM) molecules that specifically bind Aβ1-42 peptides from pooled human plasma comprising:
   (a) performing a first caprylate precipitation such that a first precipitate and a first supernatant comprising immunoglobulins are formed;
   (b) separating the first supernatant from the first precipitate;
   (c) performing a second caprylate precipitation such that a second precipitate and a second supernatant comprising immunoglobulins are formed;
   (d) separating the second supernatant from the second precipitate;
   (e) contacting the second supernatant with a first anion exchange resin;
   (f) separating a fraction containing substantially all of the immunoglobulin G and immunoglobulin M from the result of step (e);

(g) contacting the fraction of step (f) with a second anion exchange resin;
(h) eluting IgM from the second anion exchange resin column;
(i) applying the IgM to a gel filtration resin and recovering the IgM;
(j) applying the IgM to an affinity resin comprising immobilized antigens A and B; and
(k) recovering the eluted IgM to obtain a purified, virally inactivated IgM preparation.

2. The method of claim 1, wherein the immunoglobulin preparation comprises at least about 80% IgM or at least about 90% IgM.

3. The method of claim 1, wherein the IgM has a titer of specific binding for an Aβ1-42 peptide that is at least 10-times higher than that for an Aβ1-40 peptide.

4. The method of claim 1, wherein the immunoglobulin preparation comprises less than 5% oligomeric IgM.

5. The method of claim 1, wherein the IgM is a monomeric or proteolytic fragment of IgM that specifically binds an Aβ1-42 peptide.

6. The method of claim 1, further comprising:
(a) identifying a patient having an increased risk of developing or showing symptoms of a disease associated with β-amyloid polypeptides; and
(b) administering to the patient an effective amount of the immunoglobulin preparation.

7. The method of claim 6, wherein the effective amount is about 0.1 μg per kg body weight to about 1000 mg per kg body weight.

8. The method of claim 6, wherein the effective amount is about 0.5 μg per kg body weight to about 500 mg per kg body weight; about 0.5 μg per kg body weight to about 100 mg per kg body weight; or about 5 μg per kg body weight to about 50 mg per kg body weight.

9. The method of claim 6, wherein the step of administering comprises administering by a parenteral route.

10. The method of claim 6, wherein the disease associated with β-amyloid polypeptides in a patient is selected from the group consisting of systemic senile amyloidosis, familial amyloid polynephropathy (Iowa), familial amyloidosis (Finnish), Gerstmann-Straussler-Scheinker syndrome, familial amyloid nephropathy with urticaria and deafness (Muckle-Wells syndrome), isolated atrial amyloid, hemodialysis-associated amyloidosis (HAA), sporadic cerebral amyloid angiopathy, hereditary cerebral amyloid angiopathy, Downs syndrome, Parkinson-dementia of Guam, age-related asymptomatic amyloid angiopathy, hereditary cerebral hemorrhage with amyloidosis, Kuru, Creutzfeldt-Jacob's disease, Parkinson's Disease, Huntington's chorea, and Alzheimer's disease.

* * * * *